(12) United States Patent
Openshaw

(10) Patent No.: US 11,464,478 B2
(45) Date of Patent: Oct. 11, 2022

(54) METHOD AND SYSTEM OF ASSESSING OR ANALYZING MUSCLE CHARACTERISTICS INCLUDING STRENGTH AND TENDERNESS USING ULTRASOUND

(71) Applicant: SONOGRADE INC., Davis, CA (US)

(72) Inventor: John Openshaw, Modesto, CA (US)

(73) Assignee: SONOGRADE INC., Davis, CA (US)

( * ) Notice: Subject to any disclaimer, the term of this patent is extended or adjusted under 35 U.S.C. 154(b) by 0 days.

(21) Appl. No.: 14/710,468

(22) Filed: May 12, 2015

(65) Prior Publication Data

US 2015/0323503 A1    Nov. 12, 2015

Related U.S. Application Data

(60) Provisional application No. 61/992,021, filed on May 12, 2014.

(51) Int. Cl.

| | |
|---|---|
| *A61B 8/08* | (2006.01) |
| *A61B 5/22* | (2006.01) |
| *A61B 5/00* | (2006.01) |
| *G01N 29/04* | (2006.01) |
| *G01N 29/06* | (2006.01) |

(52) U.S. Cl.
CPC ............... *A61B 8/08* (2013.01); *A61B 5/224* (2013.01); *A61B 5/4872* (2013.01); *A61B 5/7275* (2013.01); *A61B 8/0858* (2013.01); *G01N 29/043* (2013.01); *G01N 29/0654* (2013.01); *A61B 2503/10* (2013.01); *A61B 2503/40* (2013.01); *G01N 2291/017* (2013.01); *G01N 2291/02475* (2013.01); *G01N 2291/02818* (2013.01); *G01N 2291/02854* (2013.01)

(58) Field of Classification Search
None
See application file for complete search history.

(56) References Cited

U.S. PATENT DOCUMENTS

| | | |
|---|---|---|
| 5,685,307 A | 11/1997 | Holland et al. |
| 6,167,759 B1 | 1/2001 | Bond et al. |
| 6,170,335 B1 | 1/2001 | Clinton |
| 7,444,961 B1 | 11/2008 | Ellis |
| 8,494,226 B2 | 7/2013 | Wilson et al. |
| 2004/0024312 A1 | 2/2004 | Zheng |
| 2009/0216459 A1 | 8/2009 | Goldberg et al. |
| 2010/0158874 A1 | 6/2010 | Rogers et al. |

OTHER PUBLICATIONS

Hiblar et al. Database Medline, AN 2004201083 ( Advances in experimental medicine and biology, (2003) vol. 538, pp. 635-644).*
Pagonidis et al. Journal of Computer Assisted Tomography, 29(1), 2005, pp. 108-111.*
Totland et al. Meat Science 23, Issue 4, 1988, pp. 303-315 (see Abstract).*
Albrerch et al. J Anim Sci. 2006,84(11):2959-2964.*
Wilson DE. Application of ultrasound for genetic improvement. Database Medline PMID: 1564015 (J Anim Sci. Mar. 1992;70(3):973-983).*
Narici. Journal of Electromyography and Kinesiology 9, 97-103, 1999.*
International Search Report and Written Opinion dated Aug. 27, 2015, regarding PCT/US2015/030398.
Turo, D et al., "Ultrasonic Tissue Characterization of the Upper Trapezius Muscle in Patients with Myofascial Pain Syndrome"; Aug. 2012; Conference Proceedings IEEE Engineering in Medicine and Biological Society; 2012 4386-4389.
Gao, Yet al. "Age-related changes in the mechanical properties of the epimysium in skeletal muscles of rats", 2008, Journal of Biomechanics; 41 (2): p. 465.
Ph et al., "Characterization of lamina propria and vocal muscle in human vocal fold tissue by ultrasound Nakagami imaging", 2011, Medical Physics 38, pp. 2019-2024.
Atkinson, RA et al., "Effects of Testosterone on Skeletal Muscle Architecture in Intermediate-Frail and Frail Elderly Men", Nov. 2010, Journal of Gerontology, 65A (11): 1216-1217.
Williams, PE et al., "Changes in sarcomere length and physiological properties in immobilized muscle", 1978, Journal of Anatomy 127 (3): p. 467.
Reeves, ND et al., "In vivo human muscle structure and function: adaptations to resistance training in old age", Nov. 2004, Experimental Physiology, 89(6): 675-676.

\* cited by examiner

*Primary Examiner* — Michael L Borin
(74) *Attorney, Agent, or Firm* — Procopio, Cory, Hargreaves & Savitch LLP

(57) ABSTRACT

A method and system of predicting a muscle characteristic using ultrasound. The characteristic may include a tenderness characteristic and/or a strength characteristic. An analysis of muscle structure is performed for a sample using ultrasound data of the sample. The analysis may include determining a relative number of bundles, fascicles, sarcomeres, fibers, and/or sheath thickness from the ultrasound data. Thereafter, the muscle characteristic is predicted for the sample based on the analysis.

31 Claims, 16 Drawing Sheets

1202
striations showing
bundles 1304 striations showing fascicles  1302 striations showing bundles

METHOD AND SYSTEM OF ASSESSING OR ANALYZING MUSCLE CHARACTERISTICS INCLUDING STRENGTH AND TENDERNESS USING ULTRASOUND

CROSS-REFERENCE TO RELATED APPLICATION

This application claims the benefit of U.S. Provisional Application Ser. No. 61/992,021, entitled "Method and System of Assessing or Analyzing Muscle Characteristics Including Strength and Tenderness Using Ultrasound" and filed on May 12, 2014, which is expressly incorporated by reference herein in its entirety.

BACKGROUND

Field

The present disclosure relates generally to the field of diagnostic sonography imaging and techniques, more particularly, to a method and system for analyzing ultrasound images for muscle tissue density, tensile strength and mass, as well as, equating it into a rating of palatability, pliability, tenderness, strength, and/or power.

Description of Related Art

Carcass evaluation, whether performed "on the hoof" for live animals or "on the rail" for hot carcass or meat has been performed phenotypically and by using ultrasound. A Quality grade, such as "prime," "choice," or "select," may then be designated to the carcass based on the pheno evaluation. Ratings may also be designated for livestock carcass evaluation. It is very important to the meat and livestock industry to have a system that can provide an objective measurement of carcass and meat quality. Pliability or tissue tenderness is a highly desired quality. The United States Department of Agriculture (USDA), e.g., applies techniques to grade beef based on assessment of adipose tissue content within the muscle known as intramuscular fat (IMF), e.g., "marbling." However, marbling often fails to accurately predict tenderness because there are two types of tissue. Additionally, the current USDA Quality Grade and Yield Grading system that correlates high fat content with tenderness can discourage meat consumption in a health conscious consumer base.

Although various ultrasound-based technologies have been used for carcass evaluation, this technology has a direct correlation to the measurement of, the amount of back fat, rib-eye area, and IMF known as Marbling. There continues to be a need for a more accurate analysis pertaining to muscle density, mass, tissue pliability, and tissue texture separate from the assessment of taste and palatability, currently known as quality grade.

SUMMARY

In light of the above described problems and unmet needs, as well as others, in an aspect of the disclosure, a method, a system, and/or a computer program product are provided that provide and/or predict a more accurate analysis of muscle structure in its complex form. Aspects presented herein further provide the capability to analyze tissue palatability, which relates to muscle pliability and tenderness, separate from an assessment of fat, e.g., IMF. Currently, meat, such as steaks, which have a combination of low fat content and good pliability values, cannot be predicted in livestock. Aspects presented herein provide a method and system to perform noninvasive evaluation on live, on the rail, or packaged meat to characterize taste and palatability, including pliability and tissue tenderness. This includes identifying animals that are more likely to have a desirable consumer experience, e.g., that allows a consumer to enjoy a delectable delicious charbroiled, seasoned to perfection cooked rib-eye steak.

Thus, aspects presented herein provide a method and system for analyzing ultrasound images in order to identify muscle tissue, density, tensile strength and mass, as well as, equating or otherwise correlating such analyses to a rating of tenderness with the quality grade. This functionality may include grading muscle structure of all muscle groups. The number of muscle bundles, sarcomeres, fascicles, fibers, sheaths around these aspects and/or muscle break down may be analyzed and ratings may be generated for muscle strength, growth, and/or tissue pliability, e.g., tenderness.

An analysis of the muscle structure may be performed via a simple scanning procedure using ultrasound equipment to collect imaging data for evaluation. For example, the ultrasound equipment and settings that enable an accurate image at a depth of approximately between one to three inches of tissue, e.g., approximately two inches deep into the analyzed tissue, may be performed.

The analysis may include determining a relative number of bundles within a muscle group, such as by using ultrasound equipment. Aspects may include gathering data in determining a relative number of fascicles, sarcomeres, and or fibers within the bundle, including measurements of the epimysium, endomysium, or sheaths around each structure of muscle from the ultrasound image.

Thereafter, a number of muscle characteristics may be determined or predicted based on the analysis. For example, muscle pliability, or softness, may be predicted for the sample based on the analysis. Additionally, other characteristics, including a potential for strength in competing subjects, whether human or competition animals, may be predicted based on the analysis. For example, the analysis may be used for person involved in sports competitions and athletic events. This analysis may be performed regardless of the age of the subject, due to the fact that each animal is predisposed to have at birth a given amount of muscle tissue and may never produce any more for the rest of its life.

Aspects may further include using a rating system that can identify the quality grade for cuts of meat having a desirable amount of palatability even with moderate or lower fat content.

Additional advantages and novel features of these aspects will be set forth in part in the description that follows, and in part will become more apparent to those skilled in the art upon examination of the following or upon learning by practice of this diagnostic or sonographic analyses program and invention and aspects thereof.

BRIEF DESCRIPTION OF THE DRAWINGS

Various example aspects of the systems and methods will be described in detail, with reference to the following figures, wherein.

DETAILED DESCRIPTION

These and other features and advantages are described in, or are apparent from, the following detailed description of various example aspects. The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

As presented herein muscle characteristics may be determined or predicted based on an analysis of ultrasound images of the muscle. For example, any of muscle palatability, pliability, texture, tenderness, and/or softness, can be predicted for the sample based on the analysis. These characteristics are also referred to herein as tissue characteristics. Additionally, other characteristics, including a potential for strength and/or power in competing or sporting subjects, whether human or competition animals, may be predicted based on the analysis.

Tenderness

Currently, livestock and on the rail product are rated based on quality grade and yield grade by a USDA inspector performing a phenotypical analysis of fat found on and within the carcass, e.g., KPH fat. However, such a measurement of fat is not always an accurate predictor of tenderness, texture, pliability, tissue softness, and/or palatability of subsequently processed meat. Additionally, breeds of livestock that have lower amounts of fat will incur poor ratings, even though a number of such livestock could have a potential to be a producer of more desirable cuts of meat.

Meat palatability, pliability, softness, and/or tenderness relates to the structure of the muscle itself. Thus, aspects presented herein include performing an analysis, by the use of ultrasound and collected imaging data, e.g. analyze the muscle structure of, bundle, sarcomeres, fascicles, and fibers within the deposition of the muscle, by collecting ultrasound images to predict tenderness of the muscle and muscle strength. For example, the analysis may include determining or counting a number of bundles, a number of fascicles, a number of sarcomeres, and/or a number of fibers within the muscle, as well as measuring sheath(s) that surround each component of muscle in order to determine a score, e.g., a toughness score.

Figure 1:
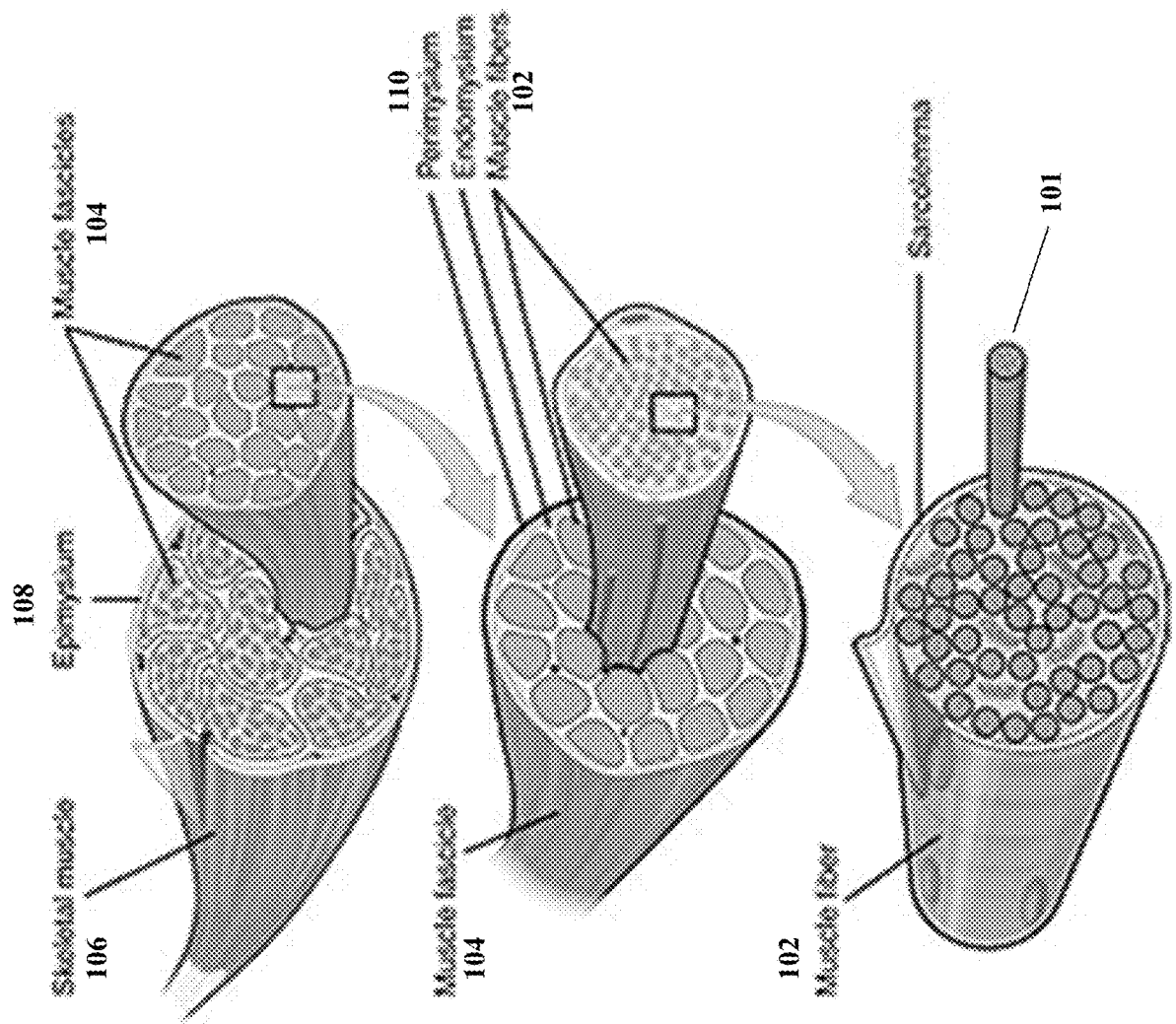
FIG. 1 is a diagram illustrating an example of muscle structure, in accordance with aspects of the present invention.

Skeletal Muscles are structured within a bundle inside of bundles within the muscle tissue. As illustrated in FIG. 1, a sarcomere is the basic unit of a muscle. Muscles are composed of tubular muscle fibers 102 (myocytes or myofibers) that are in turn composed of tubular myofibrils. Myofibrils are composed of repeating sections of sarcomeres. Sarcomeres are composed of long, fibrous proteins that slide past each other when the muscles contract and relax. The striated appearance of skeletal muscle results from the regular pattern of sarcomeres within their cells. A muscle fiber 102 may contain any number of sarcomeres. Thus, a muscle fiber 102 comprises bundles of sarcomeres, and the muscle fibers 102 are bundled into a group to form a fascicle 104. Bundles of fascicles 104 then form the overall muscle 106.

Skeletal muscles, such as those found in livestock, are sheathed by a tough layer of connective tissue called the epimysium 108 and a matrix of the sheath. Each epimysium 108 comprises multiple fascicle bundles 104, each of which contains a number of muscle fibers 102 collectively sheathed by a perimysium 110. Each muscle fiber 102 comprises bundles of sarcomeres, which can be measured as an aspect in a prediction or rating relating to tenderness.

The number of these bundled fibers varies significantly among different subjects, even subjects of the same species. For example, each bundle may comprise a range of fascicles, and fibers, right down to the sarcomeres, held together by a matrix of Perimysium, Endomysium, and Epimysium. e.g., approximately between 10 and 500 plus.

Figure 2:
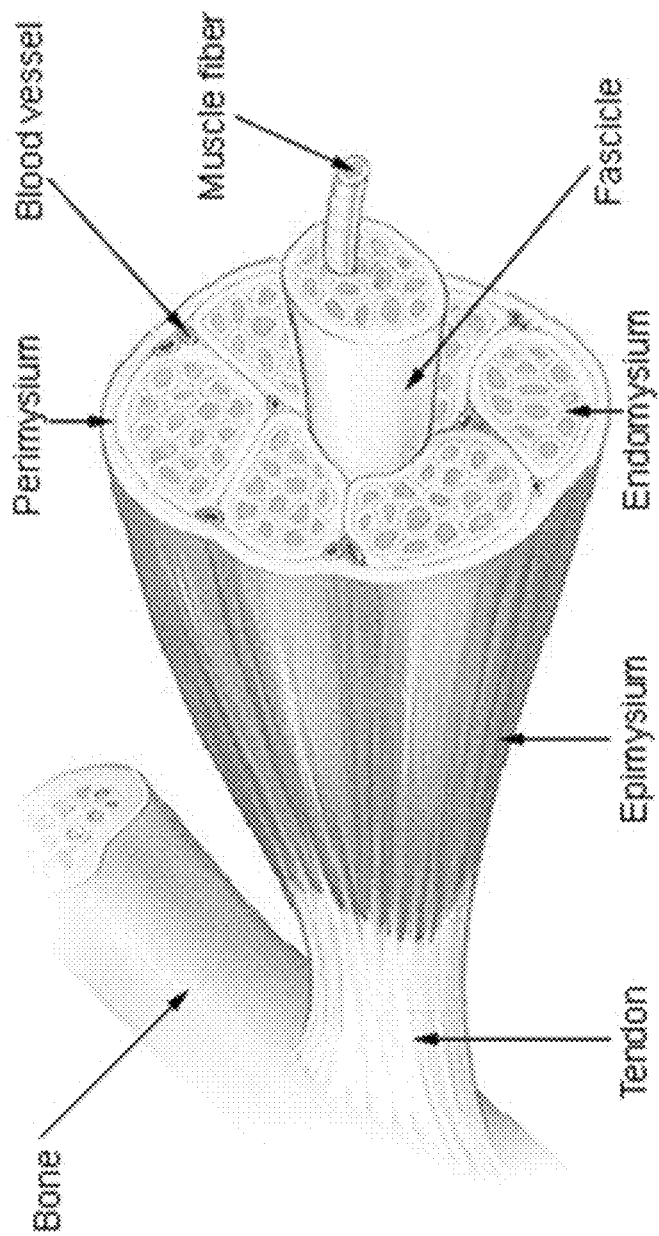
FIG. 2 is a diagram illustrating an example of muscle structure, in accordance with aspects of the present invention.

FIG. 2 provides two modalities of muscle structure, sagittal and transverse.

Additional details regarding muscle structure may be found, for example, published on Wikipedia webpages under the designation "muscle" and "sarcomere," which is located at http://en.wikipedia.org/wiki/Muscle and http://en.wikipedia.org/wiki/Sarcomere, respectively, the entire contents of which are hereby incorporated herein by reference.

Figure 11:
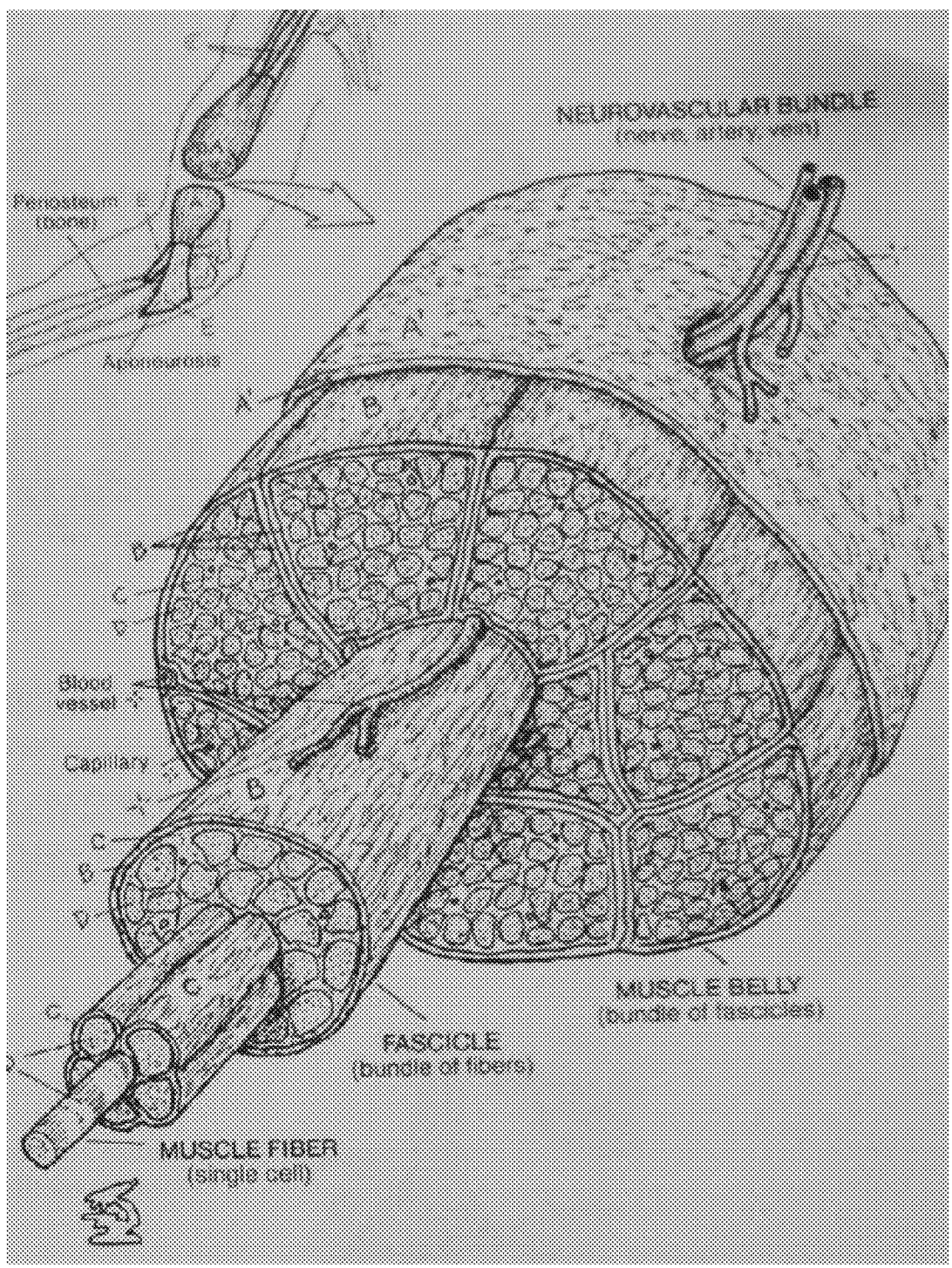
FIG. 11 is a diagram illustrating an example of muscle structure, in accordance with aspects of the present invention.

FIG. 11 contains an additional illustration of muscle structure from "The Anatomy Coloring Book" by Wynn Kapit and Lawrence M. Elson, Published in 2002 at page 44, the entire contents of which are incorporated by reference herein. Fat deposits flow in the same area as blood flow throughout the muscle structure. The analysis described herein analyzes the muscle structure, e.g., including density, size, and number of components that form a muscle structure. In areas that lack fascicles, etc., additional area may be provided for deposition of fat. The deposition of fat is currently used as a standard for quality grade to predict taste and palatability. The lack of muscle structure, e.g., fascicles within a bundle, as analyzed using the aspects presented herein, may be used to more accurately determine palatability, pliability, and tenderness.

Tough muscle typically has a coarser structure having a lower number of larger sized bundles, sarcomeres, fascicles, and/or fibers in comparison to tender muscle. The number of bundles, fascicles, sarcomeres, and/or fibers along with the coarseness of the muscle structure create stronger or weaker muscle tissue. For example, a bundle having a finer (less coarse) structure and therefore a higher number of smaller fibers, sarcomeres, and/or fascicles in bundles of muscle structure may be predicted to create stronger tissue and to have a more tender quality. For example, livestock with a finer muscle structure may be rated to be a higher quality and more likely to be tender than those with a coarse muscle structure. Coarser muscle tissue equates to tougher pieces of meat. Therefore, meat comprising a smaller more refined sized, finer fascicles and/or sarcomeres will be more tender. The number of sarcomeres and fascicles within the bundles of muscles do not change. Animals are allotted with a certain amount at the time of birth. This number does not change through the life of that animal. This characteristic occurs for all skeletal muscle tissue.

Therefore, aspects presented herein provide for a way to analyze muscle structure and tenderness separately from the current grading system of quality grade for any muscle group, which measure fat. Ultrasound is used to perform an analysis of characteristics of the muscle structure itself. As the muscle grows, e.g., the number of fascicles does not increase. Instead, the size of the individual fascicles increases. Thus, using an analysis of the relative number of fascicles and/or sarcomeres in the muscle structure may accurately predict which livestock will produce higher quality and more palatable piece of meat from a young age, because the amount of bundles, fascicles/sarcomeres does not change as the livestock matures.

Tenderness, as used herein, may relate both to subjective properties of meat tissue, such as softness, juiciness, palatability, and flavor intensity of cooked meat, as well as to an objective measure, e.g., relating to the shear and/or tensile force necessary to cut, or chew, a sample piece of meat. One example of such an objective shear force determination is the Warner-Bratzler shear (W-B shear or WBS) force values have long been used as the industry standard for an objective tenderness scale. This WBS testing has been performed only on the concept of cooked meat at 160°, then by performing the shear test without knowing the structure, volume, density, tensile or mass of the muscle tissue. Thus, there exists a need for a more accurate way of analysis with an objective determination to predict tissue palatability pliability, strength, and/or tenderness by providing a much needed scale with a greater effectiveness in selecting and developing a more accurate and consistent way of predicting palpability and tenderness.

Aspects used herein enable a comparison of muscle structure and density in a more consistent form, which also enables a higher level of accuracy, consistency, and repeatability for objective tenderness tests, such as the WBS test. For example, comparisons may be made for samples having similar muscle structure, e.g., a first sample having approximately 20 bundles, fascicles, or sarcomeres as opposed to a second sample having beyond 100 within its corresponding structure. The sample with 20 bundles, fascicles, or sarcomeres may be predicted to have less tenderness and less strength in comparison to the sample having 100.

Figure 3:
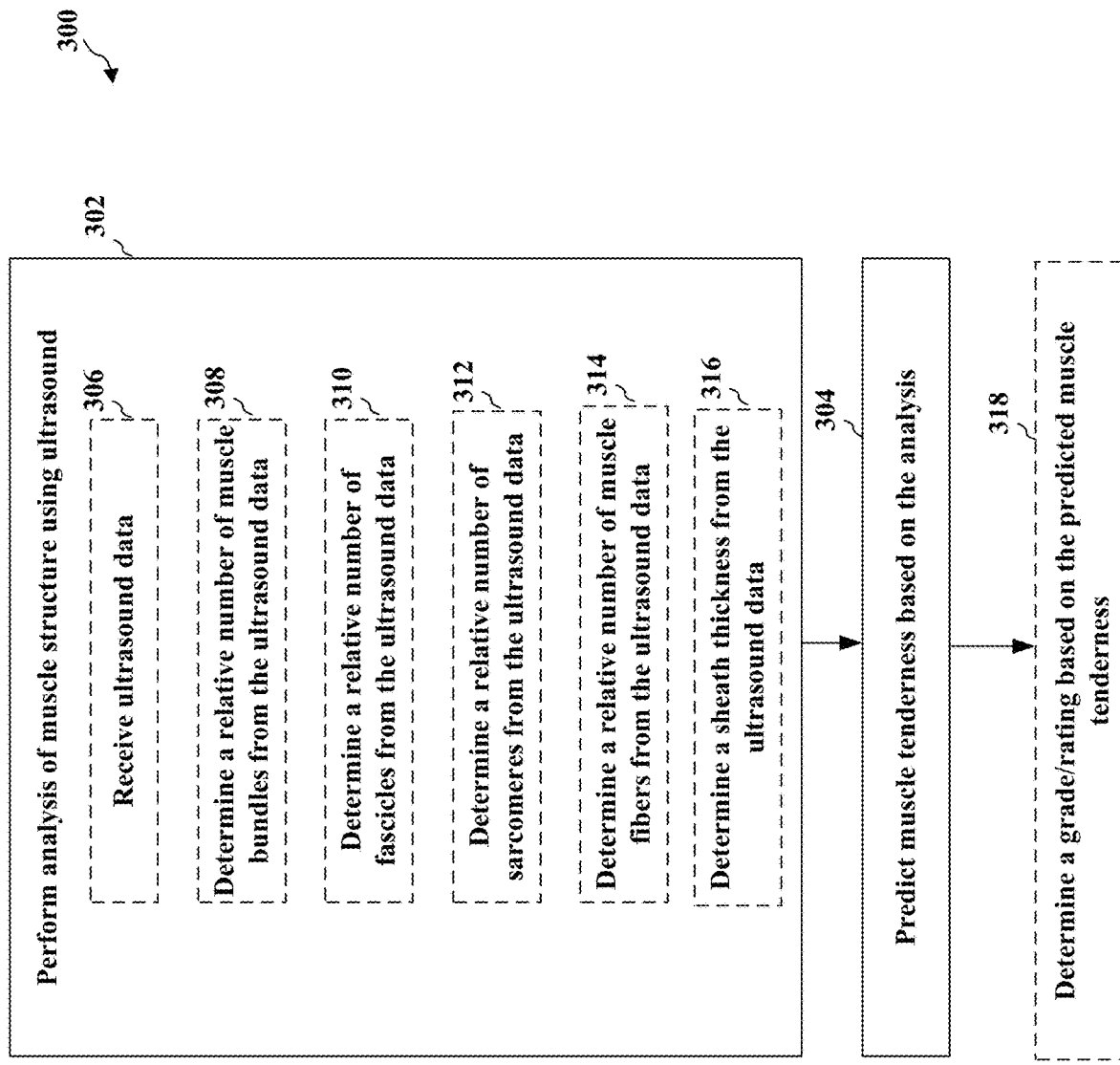
FIG. 3 is a flow chart illustrating an example method of analyzing muscle tenderness, in accordance with aspects of the present invention.
Figure 4:
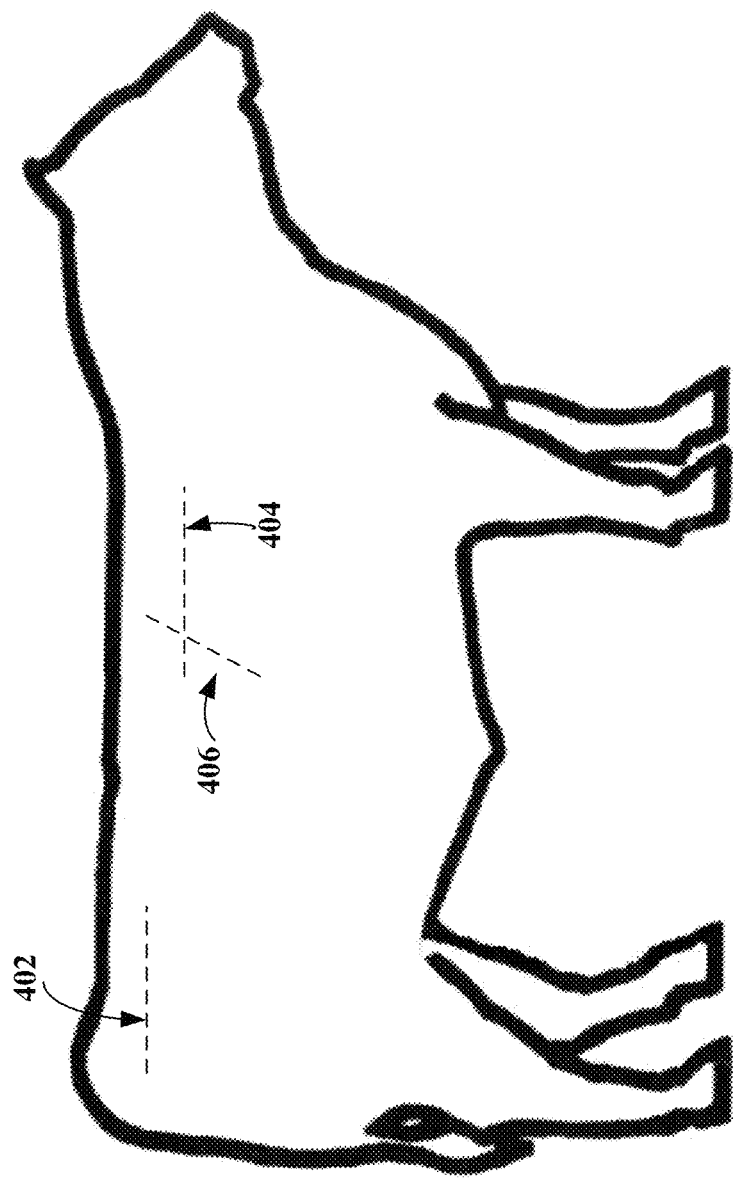
FIG. 4 is a diagram illustrating example positions for ultrasound measurements, in accordance with aspects of the present invention.

FIG. 3 is a flow chart 300 of a method of determining muscle structure, density, mass, and volume by using ultrasound. Although described using the term "muscle," this method may be used to predict tissue palpability pliability, tenderness, etc., or to provide a more efficient use of the quality grading system, rating on-the-hoof of all livestock animals, or on-the-rail for a hot carcass evaluation. Livestock may include, e.g., cattle, sheep, goats, bovine, equine, swine, etc. Although FIG. 3 is described using the example of livestock, aspects of the analysis, quality prediction, and rating in relation to the tenderness and palatability presented herein apply to any animal for which it is beneficial to evaluate and predict the quality of its meat, including e.g., aquatic animals, aviary, exotic animals, wildlife, etc. Similar to the example of evaluating livestock, it may be beneficial to evaluate and predict tissue characteristics of salmon, tuna, chicken, turkey, venison, etc. using the aspects presented herein. Additionally, although FIG. 3 is described using the example of livestock, aspects of this analysis may also be used to determine muscle strength in competing animals, including humans, as described in additional detail in connection with FIG. 5. The method may be performed by a technician and may also be performed in an automated manner, e.g., via a processor, as described infra.

At 302, an analysis is performed of muscle structure and design using ultrasound.

This may include capturing at least one image of muscle structure using ultrasound. The ultrasound image may comprise musculoskeletal ultrasound data, e.g., at least one ultrasound image captured by presenting an ultrasound probe at a desired location on any muscle group for which it is desired to know muscle tissue palpability, tenderness, and/or strength, on an animal and generating an image resultant from the ultrasound signal. Example locations are described infra, with examples shown in FIGS. 4-8.

Figure 16:
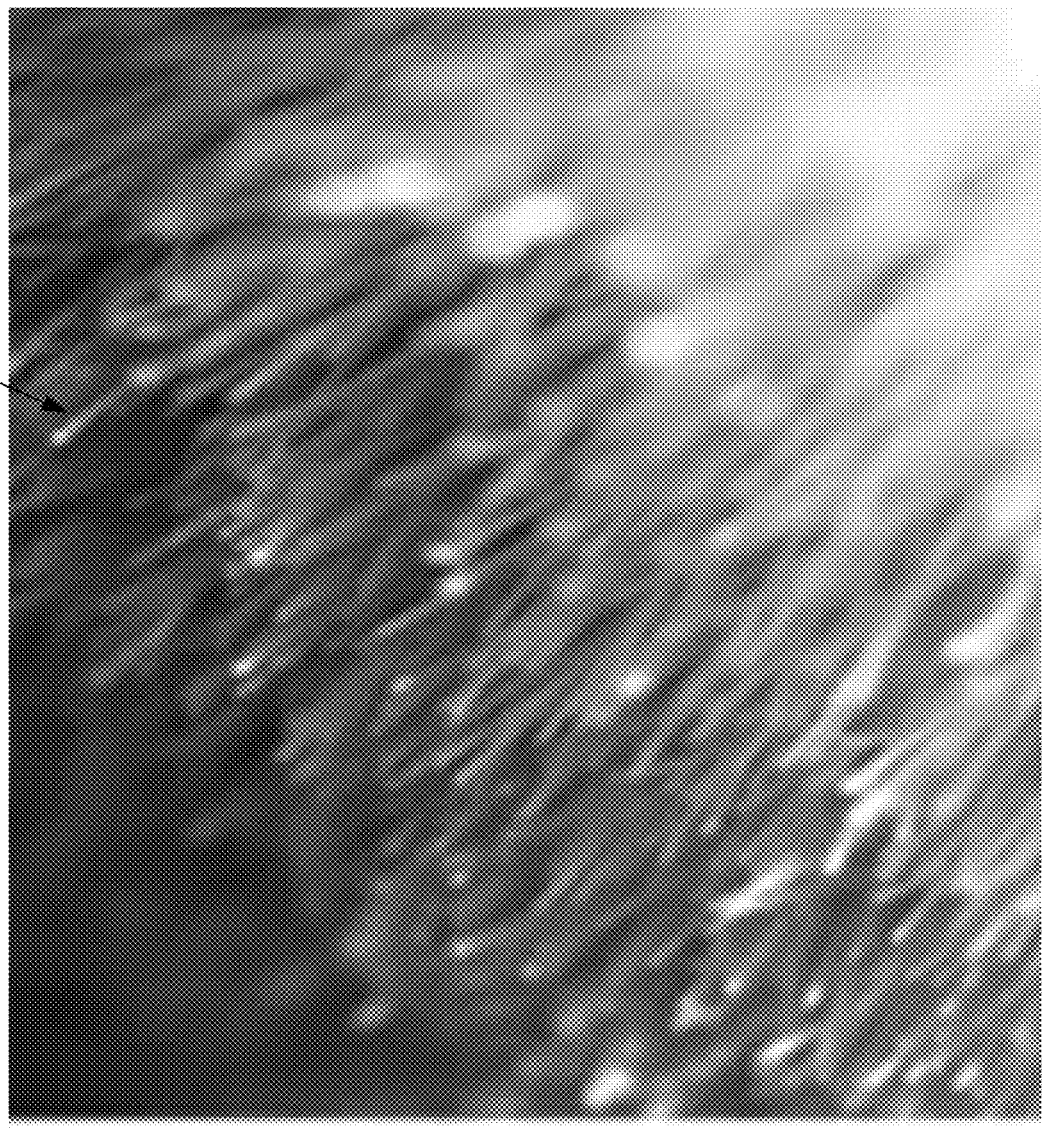

For example, the ultrasound equipment and settings that enable an accurate image at a depth of approximately between one to three inches of tissue, e.g., approximately two inches deep into the analyzed tissue, may be performed. In one example, traditional ultrasound images may be obtained. In another example, Tissue Doppler Imaging (TDI) may be used to obtain an image of the tissue. TDI uses principles similar to Doppler echocardiography to quantify high-amplitude, lower-velocity signals of myocardial tissue motion. For example, FIG. 16 illustrates a Doppler ultrasound image of muscle tissue. The Doppler ultrasound image in FIG. 16 illustrates an individual strand fiber 1602, e.g., of a ligament, can be identified, counted, measured, etc. within tissue in order to analyze the tissue characteristics such as tenderness, pliability, and strength, to determine ones susceptibility to injury, etc.

Additional example images are illustrated, e.g., in FIGS. 12-15. The ultrasound image may comprise a static image and may comprise a video of ultrasound image data so that the analysis may be made while watching movement of the muscles. Static images and video data may also be used in combination in order to perform a more accurate analysis.

The tenderness analysis in 302 may be performed for various types of samples. For example, the "sample" may be, among others, a cut of meat, an exposed portion of a carcass, or interior tissue of a live animal. The image for analysis may be manually obtained or electronically steered, e.g., steering of the sound waves.

The ultrasound data may be analyzed either at the site of the ultrasound or at a different location. If the ultrasound data is analyzed at a different location, the ultrasound data may be received via transmission and/or may be stored in memory for later analysis. For example, the analysis may be performed at a central processing location that receives and processes ultrasound data from a number of samples taken remotely from the central processing location. Thus, at 306 ultrasound data may optionally be received in order to perform the analysis. Optional aspects are illustrated using a dashed line in FIG. 3. Additional analysis may be performed on historical ultrasound image data in order to identify an inherited trend in the structure of muscle.

The analysis in 302 may include presenting ultrasound data at a display screen for evaluation by a technician, and/or analysis of the ultrasound data performed via a processor.

For example, a processor may analyze the image data generated by the ultrasound signal.

The analysis at 302 may be performed for any of a number of ultrasound techniques. Different locations on a sample may be used for the analysis, because different areas of muscle may be important for different applications. For example, different muscles may be analyzed for palatability of meat in comparison to a strength analysis for competing animals.

As illustrated in FIG. 3, the analysis of muscle structure may comprise any of determining a relative number of muscle bundles for the ultrasound data at 308, determining a relative number of fascicles within the muscle bundles at 310, determining a relative number of sarcomeres within the fascicles at 312, and determining a relative number of muscle fibers for the ultrasound data at 314.

Each of the determinations in 308, 310, 312, and 314 may include a determination of the relative size, as well as the number, of any of the muscle bundles, fascicles, sarcomeres, and fibers. The analysis is of a relative number and/or size, because any scale or rating based on such measurements must take into account the breed, age, gender, size, etc. of the animal. For example a female of a first, smaller breed may have muscle bundles and fascicles and fibers that need to be adjusted to correlate to a larger animal or breed specific measurement. Although the measurements are the same, the measurements would correlate to different levels of tenderness or muscle strength in the two animals. Thus, the breed, size, age, gender, etc. of the animal may be taken into consideration when performing the analysis.

A measurement of the matrix of the myofibril may also be taken using ultrasound and this information may be included in the analysis.

Additionally, the toughness of a sheath surrounding the muscle structure may also correlate to the strength or tenderness of the muscle. Thus, the determination may include measuring a thickness of the sheath surrounding the muscle structure, a larger, thicker sheath may correspond to a prediction of less tender meat. Thus, connective tissue, e.g., collagen, contributes to meat tenderness and texture and may strongly affect the consumer's experience. For example, such collagen, connective tissue as the perimysium, endomysium, and epimysium may be identified and measured using the hyperechoic lines within an ultrasound image. An analysis of the connective tissue may include not just a measurement of the amount or size of the tissue, but an analysis of the crosslinking of such tissue.

Any combination of determinations 308, 310, 312, 314, and 316 may be used in the analysis 302. The determination may involve counting, identifying, and/or sampling the number of bundles, fascicles, sarcomeres, and/or muscle fibers in a muscle group within the ultrasound image and corresponding data. The size of the individual bundles, fascicles, sarcomeres, and/or muscle fiber may be measured and a density may be determined. These muscle structures may be identified, measured, and counted based on an analysis of striations in the ultrasound image of the muscle. For example, FIGS. 8 and 12-14 illustrate striations that can be analyzed in order to determine or estimate muscle structure. The determination may involve estimating an amount of bundles, fascicles, and/or sarcomeres and/or measuring the sheath in the ultrasound data.

As different ultrasound images may capture larger or smaller portions of muscle, the relative number of muscle bundles, fascicles, sarcomeres, and/or fibers may be determined rather than the overall number shown in the ultrasound data. The number may be determined relative to a common amount in each muscle group. For example, a certain sample size may be considered each time. For example, the amount of such muscle structures may be identified for a two inch square sample. The size of the sample may be selected depending upon the anatomical location of the muscle being analyzed. For example, the determinations may include a determination of a density of bundles, fascicles, sarcomeres, and/or fibers and/or sheath thickness within the sample. A percentage may be generated. Additionally, a ratio may be generated relating any of the bundles, fascicles, sarcomeres, and/or fibers to one another. For example, an amount of fascicles per muscle bundle may be determined. An amount of sarcomeres per muscle bundle and/or fascicle may be determined. An amount of muscle fibers per bundle, per fascicle, and/or per sarcomere may be determined. The determined numbers may be actual numbers, estimated numbers, or average numbers of the muscle structure being identified.

At 304, a prediction may be made regarding the tenderness of the muscle based on the analysis of the ultrasound sample performed at 302. For example, a prediction of the muscle quality or tenderness may be made based on the amount of, density of, and/or size of bundles, fascicles, sarcomeres, and/or fibers identified via the ultrasound data. A tenderness scale may be provided, having a ratings corresponding to certain ranges of bundle, fascicle, sarcomere, and/or fiber measurements. For example, samples identified as having a lower coarseness fascicles and/or sarcomeres may rank higher on the tenderness scale than a sample having a higher coarseness of fascicles and/or sarcomeres. Similarly, samples identified as having a higher tissue texture coarseness may rank lower on a tenderness scale indicating a desirability of the meat.

As one example, a sample having a finer texture of bundles, fascicles, sarcomeres, and/or fibers may be considered to have an increased amount of tenderness and be ranked higher on a scale of desirable pieces of meat; whereas those with coarser bundles, fascicles, sarcomeres, and/or fibers may be considered to have a lesser degree of tenderness. Finer fibers, sarcomeres, fascicles, and bundles may be smaller in size and may also have a higher tissue density than tissue having a coarser structure. The finer tissue texture may be an indicator of tissue structure providing a more tender, palatable piece of meat, which equates to a more satisfying eating experience.

Similarly, the finer, denser muscle structure may also correlate to increased strength and a reduced susceptibility to injury.

At 318, a muscle tenderness grade and/or rating may be specified for the sample based on analyzed ultrasound data. The tenderness grade/rating may be a function of any of a density, a percentage, and a ratio of bundles, fascicles and/or sarcomeres illustrated in the ultrasound data. The rating may be similar to the choice, select, and prime designations that are used in the current quality grading system, or the rating may be completely separate from the current quality grading system. The analysis 302 and prediction 304 may be used to predict quality of livestock and yield grade.

As an additional example, the rating may provide an additional level to the current grading system. For example, the rating may involve levels, e.g., 1-5 for choice, levels 1-5 for select, and levels 1-5 for prime. Thus, a first sample may receive a rating of select, level 2 based on the analysis. A second sample may receive a rating of select, level 3. A third may receive a rating of prime, level 5.

The analysis in 302 and the rating in 318, which is based thereon, may consider other factors in connection with the analysis of muscle structure performed in 302.

For example, the analysis regarding the bundles, fascicles, sarcomeres, fibers, and/or sheaths may be used to form the basis for tenderness grading in meat samples, in combination with a consideration of the species/age of the livestock and/or traditional fat measurements, such as percentage intramuscular fat (IMF), rump fat thickness, $12^{th}$-$13^{th}$ rib fat thickness, ribeye area, marbling, etc.

For a carcass, a rating in 312 may be based on the palpability, pliability, and tenderness analysis 302 in combination with additional suitable factors including any of a type of cut of meat, electrolysis or shocking of the carcass, an aging process, heat processing, a storage temperature history, and any tenderizing treatments.

The analysis presented herein may be used to predict final carcass quality of live animals and to predict the muscle structure, volume, and mass that may be equated into tenderness of particular cuts of meat after subsequent cooking.

This carcass exam can be performed anatomically on any muscle group in any location on an animal. As each animal is predisposed with a certain muscle development at birth, they do not grow additional muscle bundles, sarcomeres, fascicles, and fibers. Evaluations "on the hoof" for live animals or "on the rail" for a carcass or meat have been performed using ultrasound. A Quality grade, such as "prime," "choice," or "select," may then be designated to the carcass based on the evaluation of each muscle group for the determination of tissue pliability and softness. Ratings, e.g., including a simple ranking such as a numerical base using a 1-5 scale, may also be designated for livestock carcass evaluation. Objective measures of carcass and meat quality may be important to the meat, but more important is having a good experience. Consumers want to know that they are purchasing a quality piece of meat each time and with each species within the meat industry. Tenderness is a highly desired quality among consumers.

Within the meat industry, the ability to accurately predict any degree of muscle palatability and tenderness is useful in a number of areas. It allows the identification of live animals having a carcass with these heritable characteristics that can be used for herd improvement. By making a determination of strength and tissue pliability based on muscle structure separately from the analysis of adipose tissue used for current standards, feeding programs may be altered and breeding programs may be designed to promote tender meat without favoring high fat content. Importantly, this approach also provides a more cost effective way to feed and raise livestock, thereby helping to keep the cost of product affordable. On the retail side, meat packers, butchers, processors and others involved in retail may use this tenderness analysis as a supplement to USDA grading to provide a more accurate prediction of quality grade or tenderness in meat. Thus, aspects presented herein may be used in combination with genetic testing and selection for breeding purposes. Aspects may include analyzing genetic test information on a group of animals and analyzing tissue structure characteristics using an ultrasound imaging of the tissue, as described herein, in order to select at least one animal from the group of animals for breeding purposes. The analysis of the tissue structure characteristics may include, e.g., analyzing the relative size, number, density, etc. of the bundles, fascicles, fibers, and/or sarcomeres. The animal may be selected from the group as being predicted to have a higher meat tenderness, strength, lowered susceptibility to injury, ability to avoid becoming a health risk, etc. than the other animals in the group. Additionally, aspects presented herein may be used in order to verify anticipated breeding results for animals identified as having a best predicted genetic potential.

Such a prediction of tenderness may be used to select a cooking technique most suitable to a specific cut of meat which may also be provided by a computer generated analysis.

Currently, USDA quality grade is mainly based on two factors: marbling and the maturity of a carcass. Current ultrasound techniques to access a visual analysis of the marbling of a sample may involve taking ultrasound images at a variety of reference points, including a rump fat measurement taken, e.g. at a rump location 402 of a sample; a $12^{th}$-$13^{th}$ Rib fat thickness taken, e.g., at 406, a ribeye area taken, e.g., at 406, and a percentage of IMF, e.g., taken at 404 in FIG. 4. Although a figure illustrating the locations for cattle is used, the ultrasound measurements and analysis may be used to determine muscle volume, density, mass, and strength in connection with any livestock breed or species.

Figure 6:
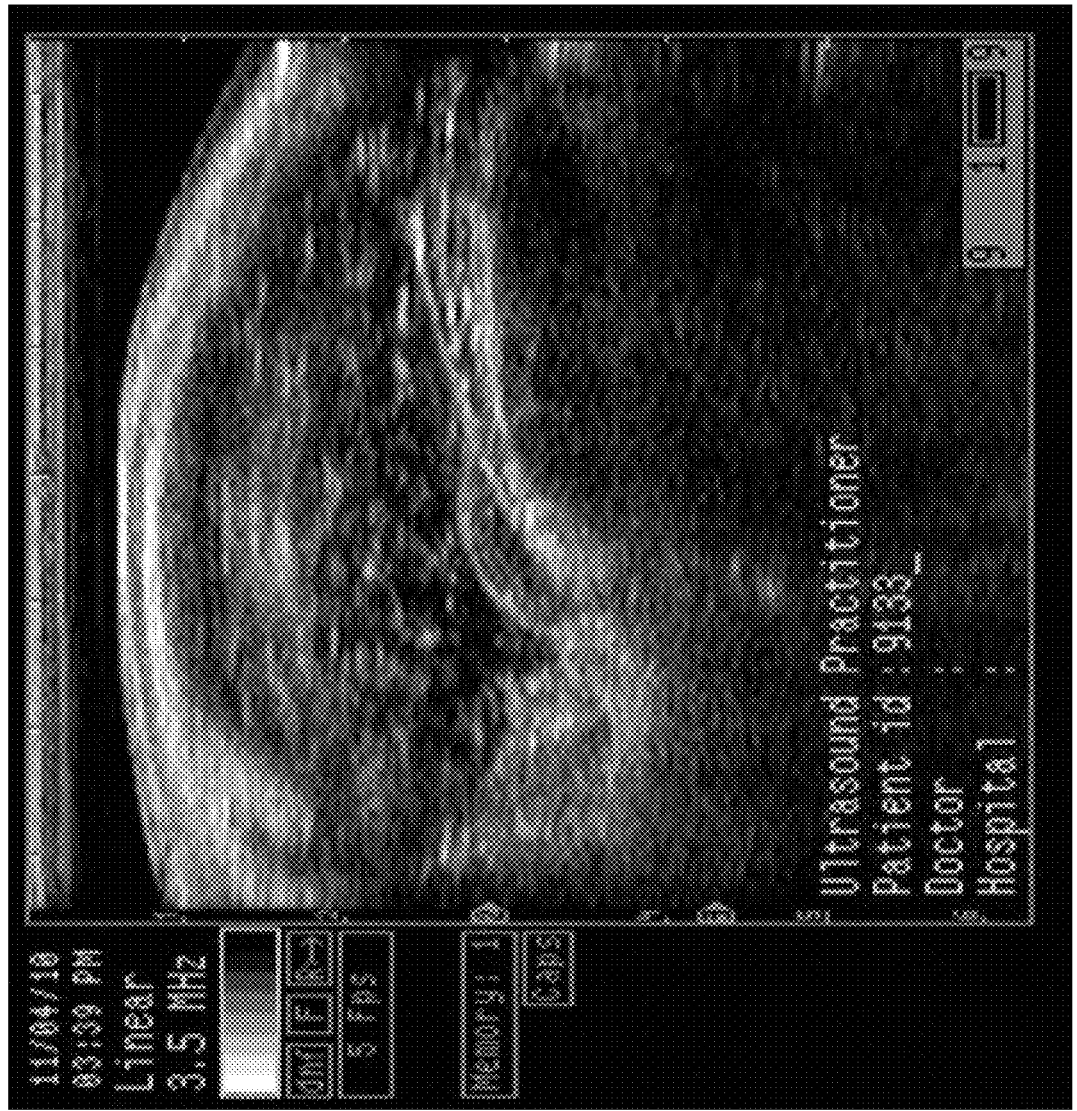
FIG. 6 is an example ultrasound image, in accordance with aspects of the present invention.
Figure 7:
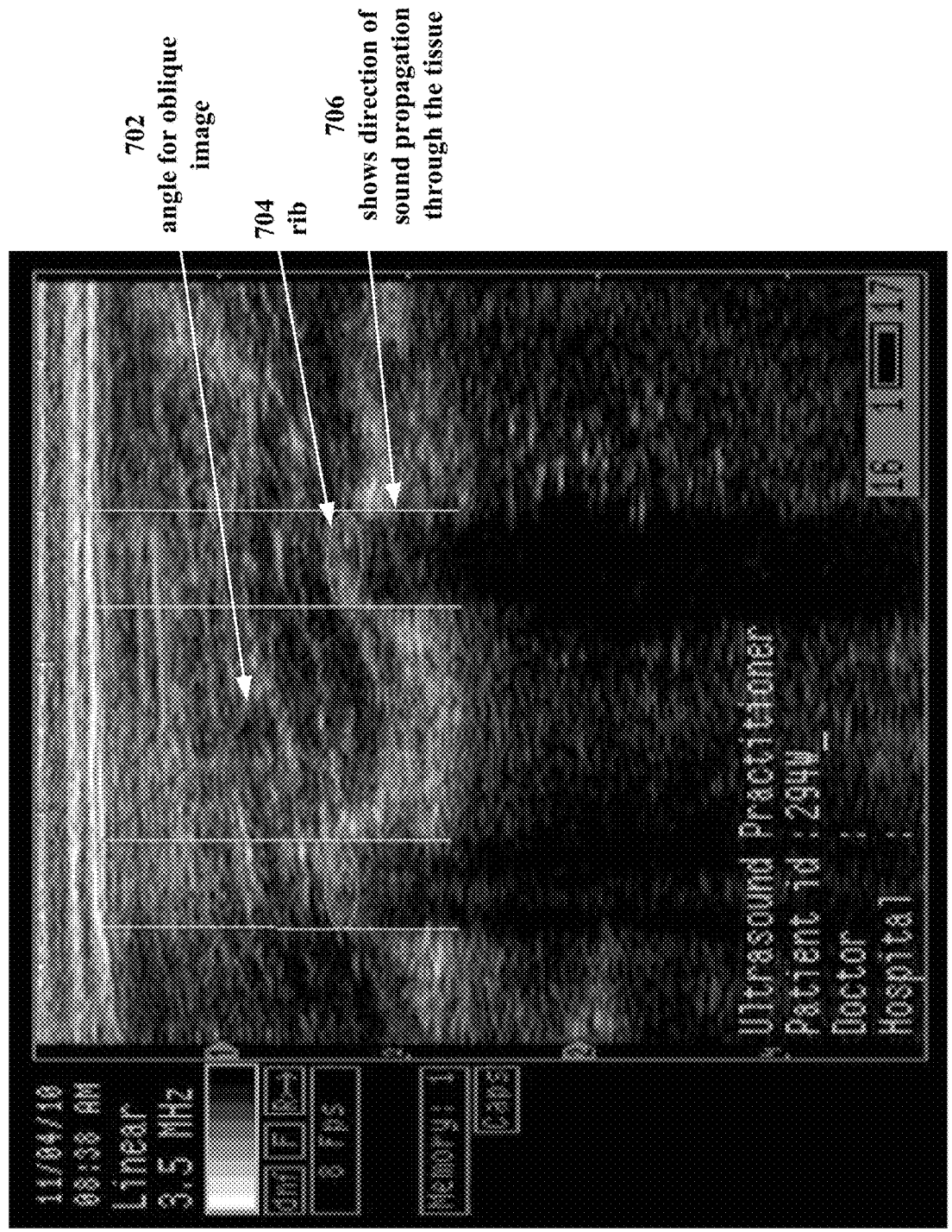
FIG. 7 is an example ultrasound image, in accordance with aspects of the present invention.

FIG. 6 illustrates an example transverse ultrasound image taken at a location between the $12^{th}$ and $13^{th}$ rib of a sample. FIG. 7 illustrates of a sagittal ultrasound image taken between a $12^{th}$ and $13^{th}$ rib of a sample. In FIG. 7, line 702 illustrates an angle for a possible oblique image. A circle is indicated at 704 to indicate the location of the $12^{th}$ and $13^{th}$ rib. These anechoic areas may be used as landmarks in order to identify the location at which an image was taken. Line 706 illustrates the direction of sound propagation through the tissue that was used to generate the image.

Figure 8:
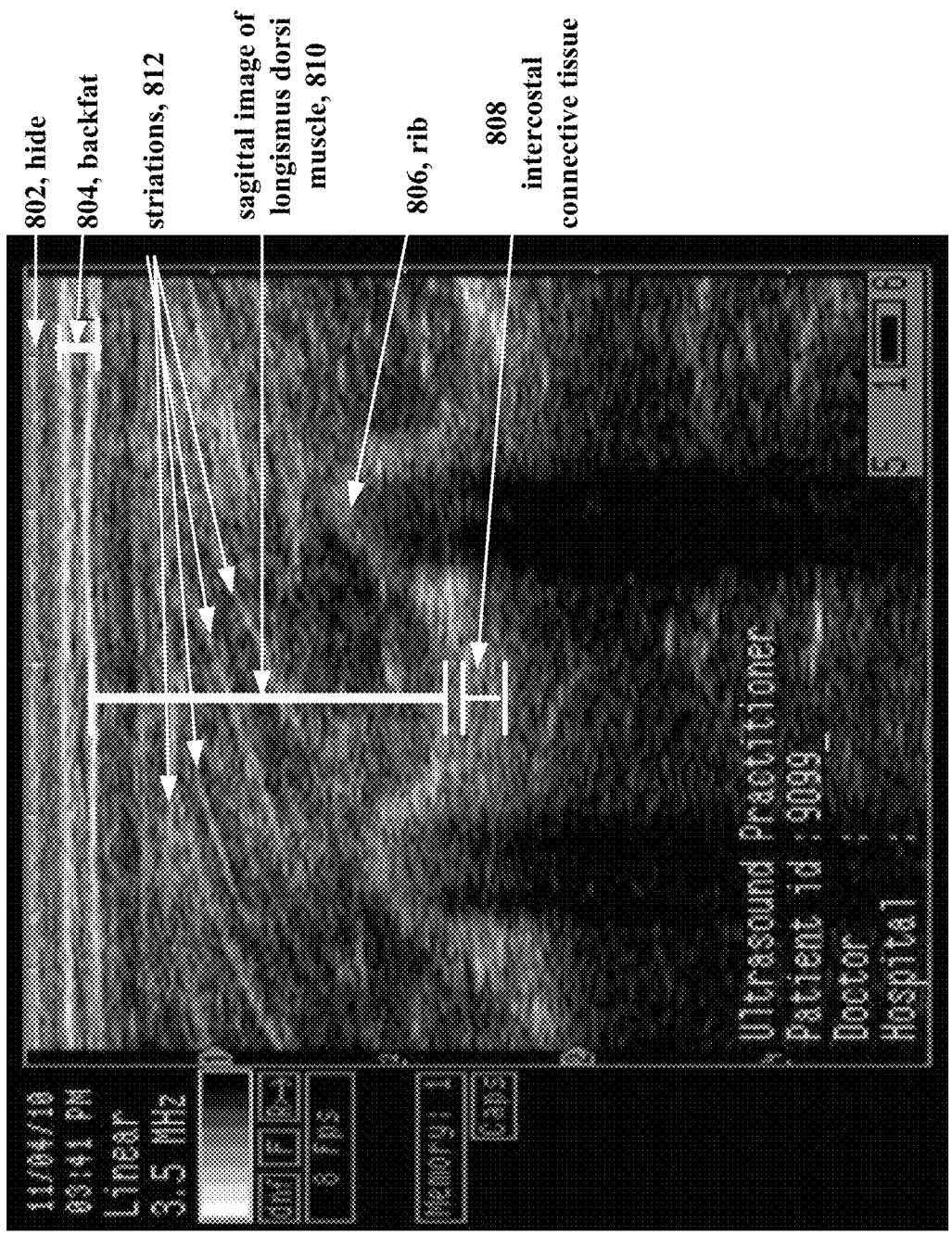
FIG. 8 is an example ultrasound image, in accordance with aspects of the present invention.

FIG. 8 illustrates another sagittal ultrasound image taken between a $12^{th}$ and $13^{th}$ rib of a sample. In FIG. 8, the image illustrates the hide 802, a backfat layer 804, longissimus dorsi muscle 810, and ribs 806. The intercostals connective tissue 808 extends between the $12^{th}$ and $13^{th}$ rib 806. The rib creates an artifact that may be used as a landmark in analysis of the image. Within the longissimus dorsi muscle 810, striations 812 provide information regarding the muscle structure.

Figure 13:
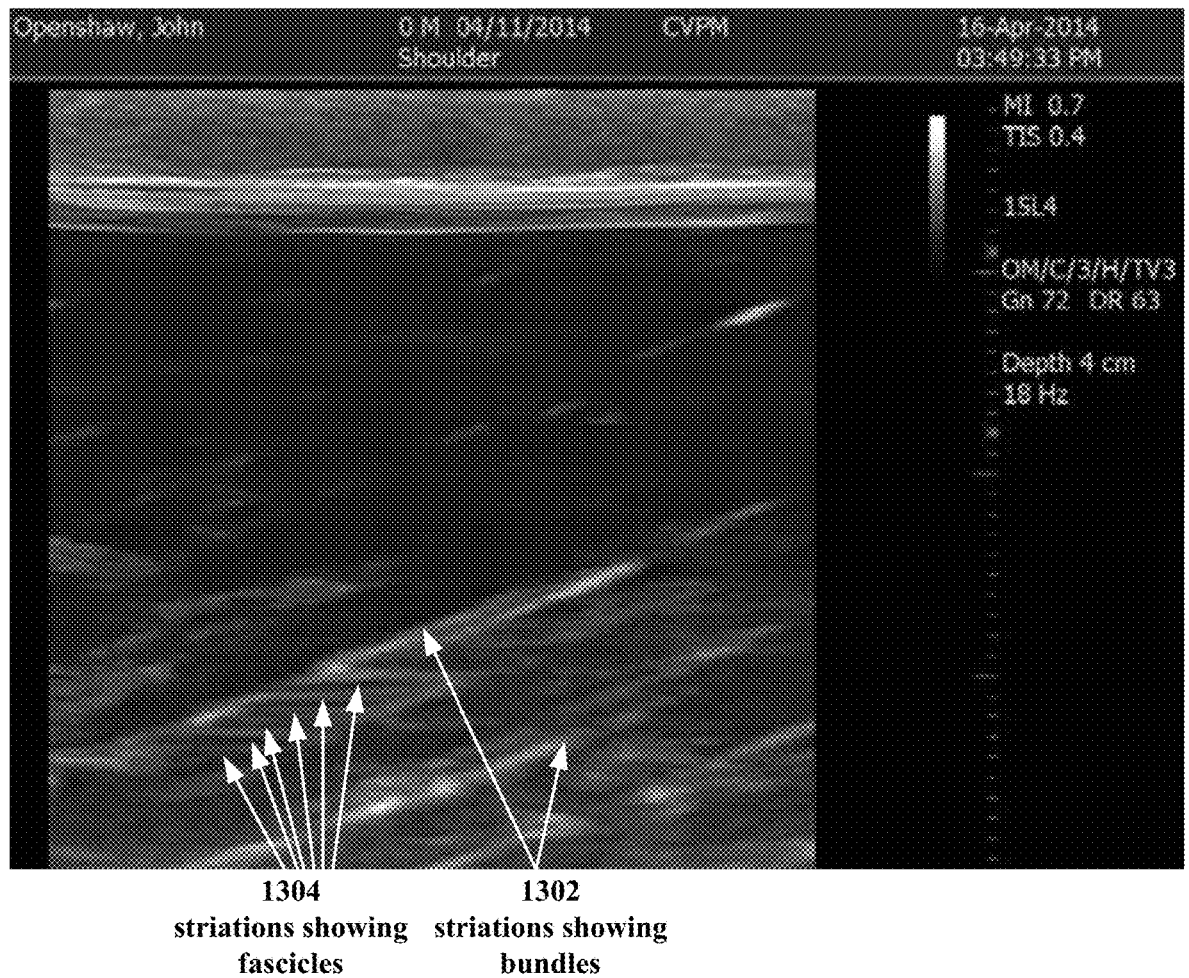
Figure 14:
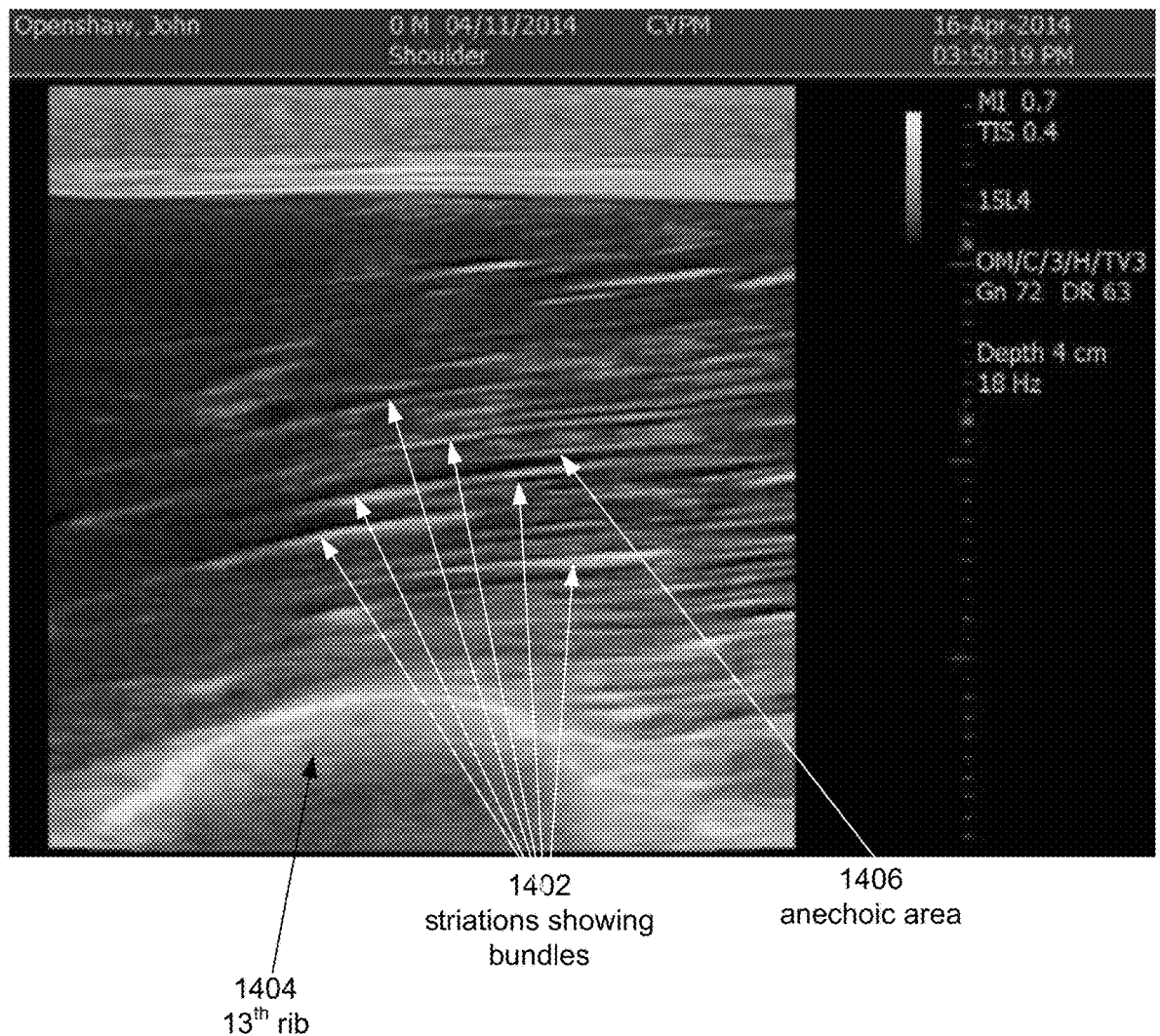
Figure 15:
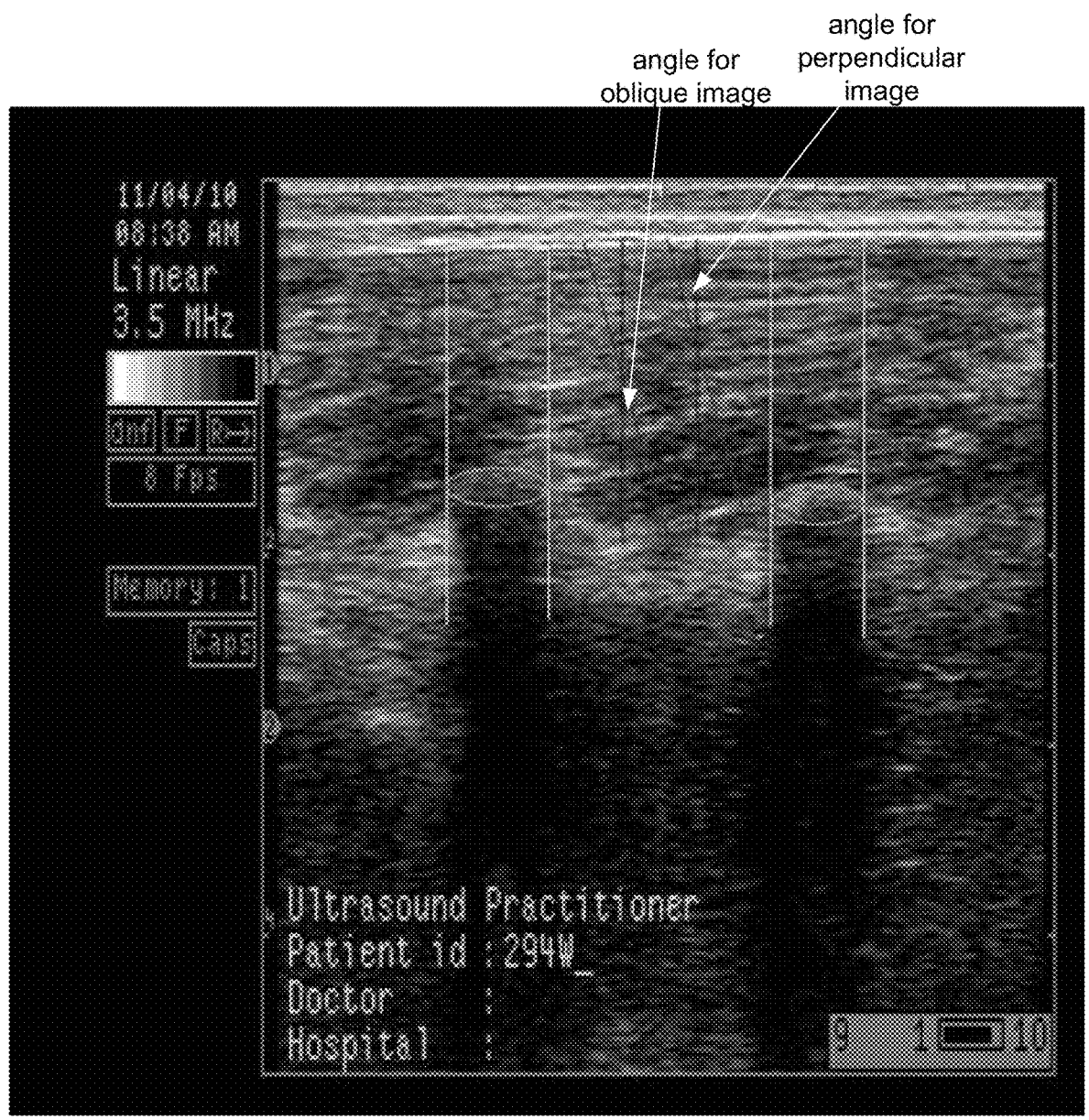

For example, the area between the striations may be used to determine the bundles within the muscle structure. FIG. 6, due to the wavelength used to obtain the image, does not enable a view of the fibers within the bundles. However, the use of different wavelengths may enable an analysis of muscle fiber. For example, FIGS. 12-14 illustrate ultrasound images taken using 18 MHz, which enables an analysis of fiber structure within the bundle of the muscle.

Thus, the analysis may include an assessment of the distance between striations in order to estimate a number of fascicles within the bundle. Additional measurements may be taken of the thickness of the striation itself. This thickness correlates to a thickness of the collagen, sheaths, epimysium, and/or connective tissues surrounding the bundle. Thus, the analysis of the muscle structure using ultrasound may include an analysis of the crosslinking and other characteristics of the collagen. Layers of collagen include the epimysium, perimysium, and endomysium. Additionally, a count may be taken of the number of striations within the image, in order to determine a count, mass, and/or density of the bundles.

The ultrasound data used to perform the analysis in 302 may be obtained using ultrasound data taken at locations similar to 402, 404, and 406 and FIGS. 5-8, as would be obtained in order to assess fat measurements.

Figure 12:
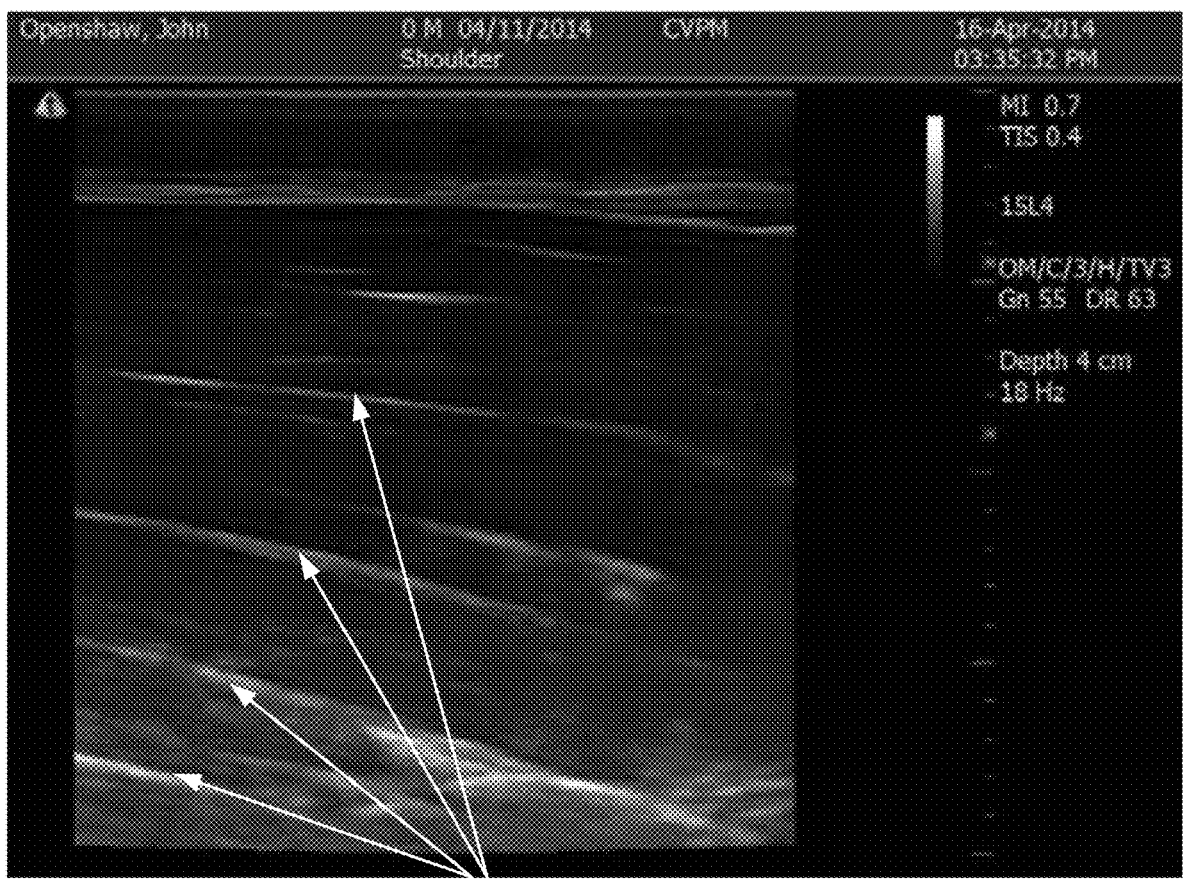
FIGS. 12-16 illustrate example images that may be used to assess characteristics of the muscle based on the muscle structure, in accordance with aspects of the present invention.

For example, FIG. 12 illustrates a sagittal ultrasound image of a sample taken near the $12^{th}$ and $13^{th}$ rib. The striations 1202 in the image may be used to estimate muscle structure, e.g. to count and/or estimate a number of bundles/fascicles/fibers and an amount of connective tissue within the muscle.

FIG. 13 illustrates an ultrasound image of a sagittal image taken at the area of the 13$^{th}$ rib. FIG. 13 includes striations 1302 that may be analyzed to determine the structure of bundles, as well as striations 1304 that may be analyzed to determine the fascicle structure within the bundles. Thus, the image may be analyzed to count the number of bundles and/or fascicles shown. Measurements may be taken of the thickness between striations in order to determine the thickness or size of the different bundles and fascicles, and measurements may be taken of the striations themselves in order to identify the size of the connective tissue surrounding the bundles and/or fascicles.

The amount of bundles and/or fascicles affects tenderness and muscle strength. Additionally, the size and amount of connective tissue affects these characteristics. For example, tougher muscle includes higher amounts of connective tissue. Thus, tender meat will include less connective tissue and smoother, less coarse structure with more amounts of bundles and/or fascicles. Thus, a more palatable piece of meat may be predicted using the analysis of the bundles, fascicles, and/or connective tissue.

In an analysis of potential strength, e.g., which may be beneficial in competing/sporting humans and animals, thicker connective tissue and higher amounts of bundles and fascicles show an increased potential for building strength.

Patterns in the striations may be breed specific. FIG. 12 illustrates a sagittal image at the 13$^{th}$ rib for a first breed, while FIG. 14 shows a sagittal image taken at the 13$^{th}$ rib 1404 for a second breed. Striations 1402 may be analyzed to determine the structure of the muscle bundles. FIG. 14 shows a higher density of bundles than FIG. 12. The image of FIG. 14 also shows striations within the bundles that indicate the structure of fascicles within the bundles. The dark or anechoic portions 1406 of the image may be used to analyze the areas between muscle structure, e.g., between fascicles. These areas may include blood and/or fat, including possible vascular systems. These areas may be used to further analyze the structure of the muscle itself.

Alternately, this procedure and analysis of the ultrasound data may be taken at different muscle groups and at any antitypical location on a sample. The analysis and processing is noninvasive to the animal and may be performed in a humane manner. Additionally, the analysis does not require the ultrasound data to be acquired at a certain age for the animal. As the muscle structure does not change through the lifetime of the animal, the ultrasound information may be gathered regardless of the age of the sample. Maturity of the sample does not affect the accuracy of the ultrasound data.

Strength Potential and Other Muscle Characteristics

Figure 5:
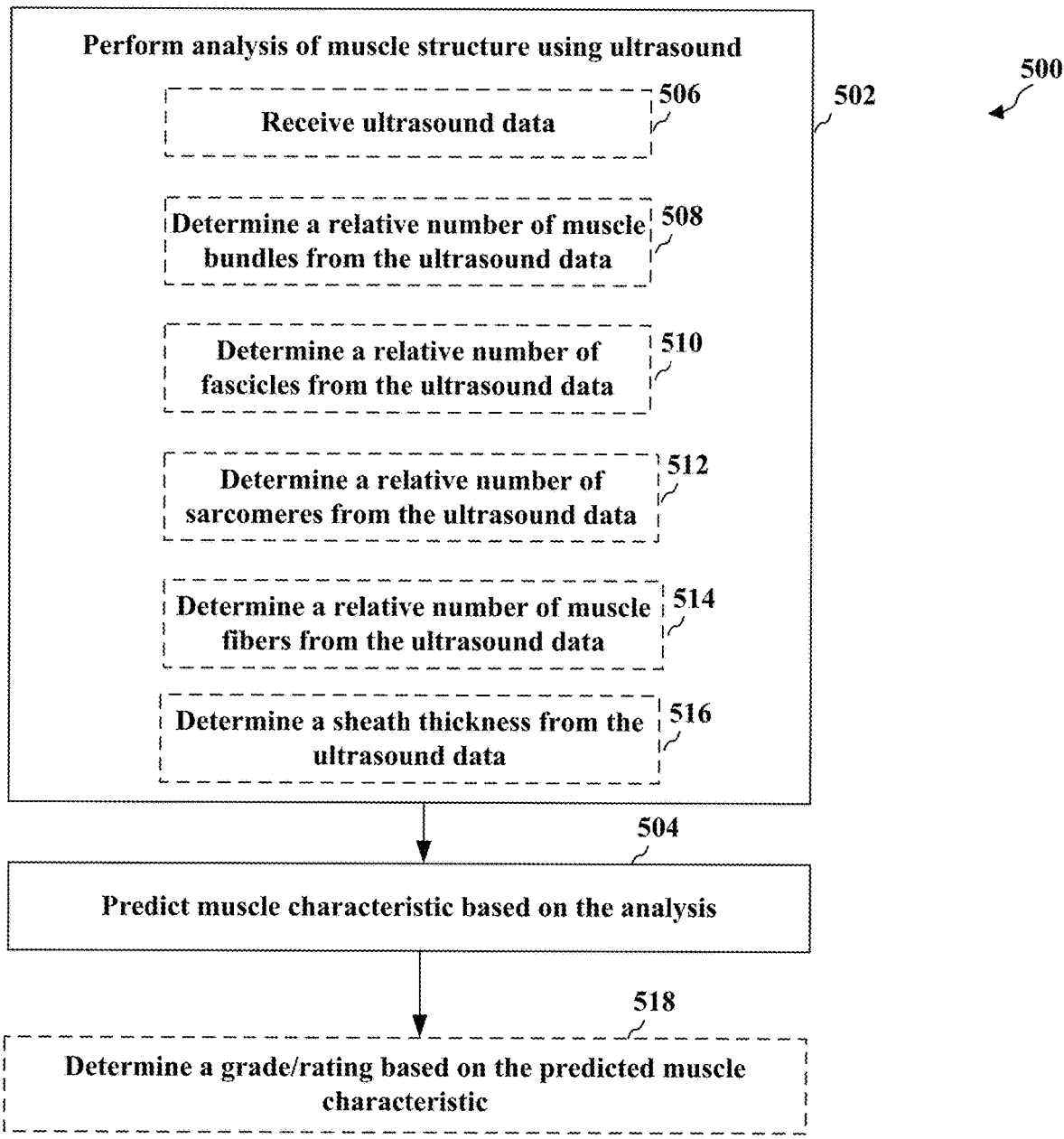
FIG. 5 is flow chart illustrating an example method of analyzing muscle characteristics, in accordance with aspects of the present invention.

An additional example is illustrated in FIG. 5. In this example, the muscle analysis may be used to identify the potential for strength and/or likelihood of susceptibility to injury rather than tenderness. This measure may be useful, for example, in competition animals that require strength for racing, jumping, lifting, etc. Such an analysis may also be useful in humans.

FIG. 5 is a flow chart 500 of a method of rating at least one muscle characteristic based on an analysis of muscle structure using ultrasound. The analyzed characteristic may be potential for muscle strength or power in animals, including humans involved in all competitions, sports, athletics, etc. The method may be performed by a technician and may also be performed in an automated manner, e.g., via a processor, as described infra.

At step 502, an analysis may be performed of muscle structure and design using ultrasound. The ultrasound image may comprise musculoskeletal ultrasound data, e.g., at least one ultrasound image captured by presenting an ultrasound probe at a desired location on any muscle group, as described in connection with FIG. 3.

At 506 ultrasound data may optionally be received in order to perform the analysis. Optional aspects are illustrated using a dashed line in FIG. 3.

As illustrated in FIG. 5, the analysis of muscle structure may comprise determining a relative number of muscle bundles for the ultrasound data at 508, determining a relative number of fascicles within the muscle bundles at 510, determining a relative number of sarcomeres within the fascicles at 512, and determining a relative number of muscle fibers for the ultrasound data at 514. Determining the relative number may include determining a size of the individual muscle structure components and/or a density or coarseness of the structure, etc. Additionally, the toughness of a sheath surrounding the muscle structure may also correlate to the strength or tenderness of the muscle. Thus, the determination may include measuring a thickness of the sheath surrounding the muscle structure. An analysis of the connective tissue or sheath may include not just a measurement of the amount or size of the tissue, but an analysis of the crosslinking of such tissue. Any combination of determinations 508, 510, 512, 514, and 516 may be used in the analysis of 502. The determination may involve counting, identifying, and/or sampling the number of, bundles, fascicles, sarcomeres, and/or muscle fibers in a muscle group within the ultrasound image and corresponding data. These muscle structures may be identified and counted via striations in the ultrasound image of the muscle, e.g., as described in connection with FIGS. 12-15. The determination may involve estimating an amount of fascicles and/or sarcomeres in the ultrasound data.

At 504, a prediction may be made regarding a characteristic of the muscle based on the analysis of the ultrasound sample performed at 502. For example, a prediction of the muscle quality or potential for muscle strength, resistance to muscle injury, etc. may be made based on the amount of bundles, fascicles, sarcomeres, and/or fibers identified via the ultrasound data. A scale may be provided, having a rating corresponding to certain ranges of bundle, fascicle, sarcomere, and/or fiber measurements. For example, samples identified as having a lower amount of fascicles and/or sarcomeres may rank lower on a scale regarding strength potential than a sample having a higher amount of fascicles and/or sarcomeres.

As one example, a sample having a larger amount of bundles, fascicles, sarcomeres, and/or fibers may be considered to have an increased amount of potential for strength when called upon, e.g., in some competition or sporting events; whereas those with a fewer amount of bundles, fascicles, sarcomeres, and/or fibers may be considered to have a reduced potential for strength.

At 518, a muscle grade or rating based on a predicted muscle characteristic may be specified for the sample based on analyzed ultrasound data. For example, the rating may relate to a predicted strength capability or to a prediction regarding the susceptibility to injury. The rating may be a function of any of a density, a percentage, and a ratio of bundles, fascicles and/or sarcomeres illustrated in the ultrasound data.

The analysis in 502 and the rating in 512, which is based thereon, may consider other factors in connection with the analysis of muscle structure performed in 502.

Although the analysis may be performed by a technician, aspects may be performed using any combination of computer hardware and/or software. For example, in one example, the analysis may be performed automatically via a processor and a tenderness rating may be output based on the analysis.

Figure 9:
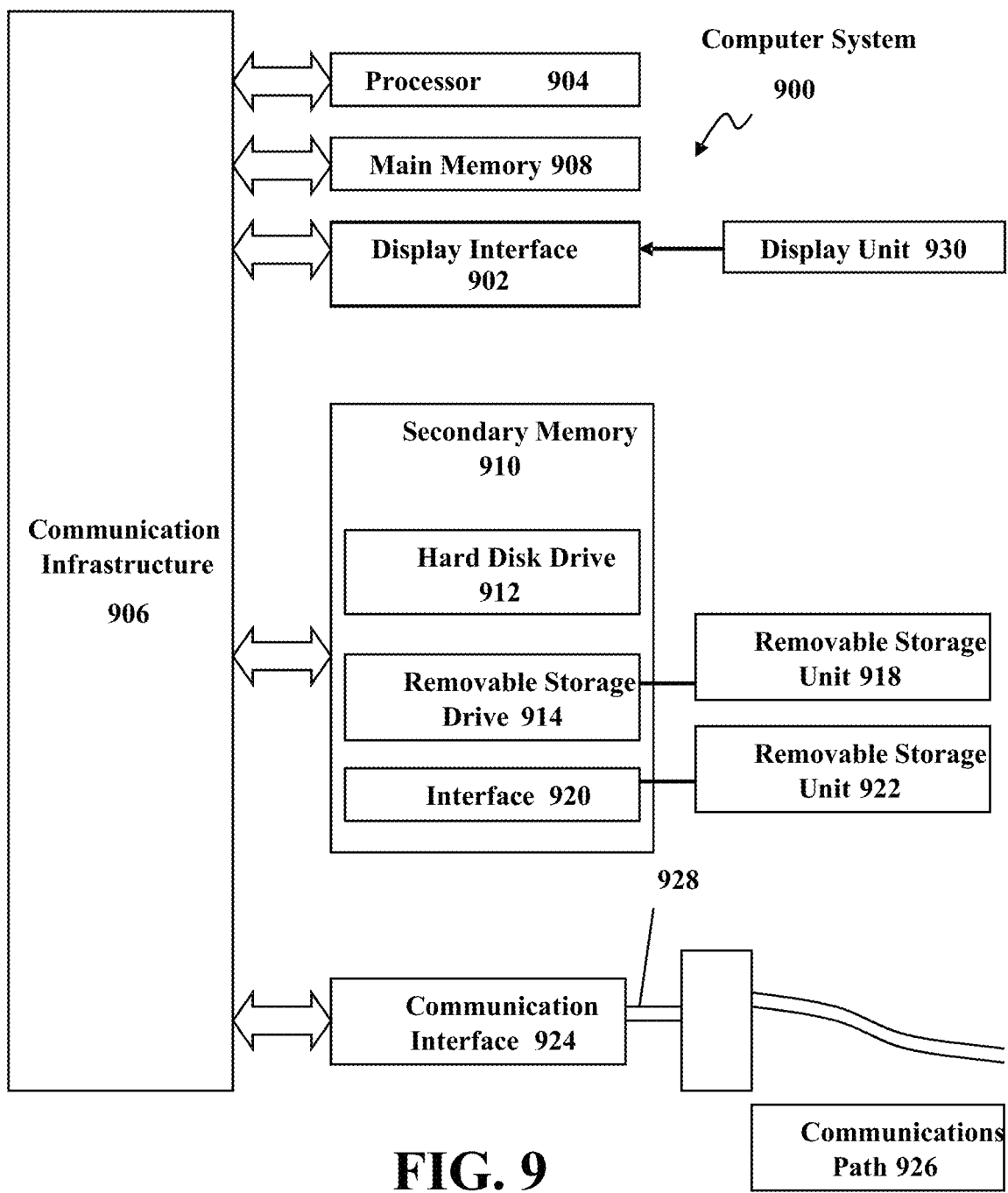
FIG. 9 presents an example system diagram of various hardware components and other features, for use in accordance with aspects of the present invention.

FIG. 9 presents an example system diagram of various hardware components and other features, for use in accordance with aspects presented herein, e.g., for performing an analysis of tenderness based on muscle structure using ultrasound. The aspects may be implemented using hardware, software, or a combination thereof and may be implemented in one or more computer systems or other processing systems. In one example, the aspects may include one or more computer systems capable of carrying out the functionality described herein. An example of such a computer system 900 is shown in FIG. 9.

Computer system 900 includes one or more processors, such as processor 904. The processor 904 is connected to a communication infrastructure 906 (e.g., a communications bus, cross-over bar, or network). Various software aspects are described in terms of this example computer system. After reading this description, it will become apparent to a person skilled in the relevant art(s) how to implement the aspects presented herein using other computer systems and/or architectures.

Computer system 900 can include a display interface 902 that forwards graphics, text, and other data from the communication infrastructure 906 (or from a frame buffer not shown) for display on a display unit 930. Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc., which is read by and written to removable storage drive 914. As will be appreciated, the removable storage unit 918 includes a computer usable storage medium having stored therein computer software and/or data.

In alternative aspects, secondary memory 910 may include other similar devices for allowing computer programs or other instructions to be loaded into computer system 900. Such devices may include, for example, a removable storage unit 922 and an interface 920. Examples of such may include a program cartridge and cartridge interface (such as that found in video game devices), a removable memory chip (such as an erasable programmable read only memory (EPROM), or programmable read only memory (PROM)) and associated socket, and other removable storage units 922 and interfaces 920, which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port, a Personal Computer Memory Card International Association (PCMCIA) slot and card, etc. Software and data transferred via communications interface 924 are in the form of signals 928, which may be electronic, electromagnetic, optical or other signals capable of being received by communications interface 924. These signals 928 are provided to communications interface 924 via a communications path (e.g., channel) 926. This path 926 carries signals 928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 980, a hard disk installed in hard disk drive 970, and signals 928. These computer program products provide software to the computer system 900. Aspects presented herein may include such computer program products.

Computer programs (also referred to as computer control logic) are stored in main memory 908 and/or secondary memory 910. Computer programs may also be received via communications interface 924. Such computer programs, when executed, enable the computer system 900 to perform the features presented herein, as discussed herein. In particular, the computer programs, when executed, enable the processor 910 to perform the features presented herein. Accordingly, such computer programs represent controllers of the computer system 900.

In aspects implemented using software, the software may be stored in a computer program product and loaded into computer system 900 using removable storage drive 914, hard drive 912, or communications interface 920. The control logic (software), when executed by the processor 904, causes the processor 904 to perform the functions as described herein. In another example, aspects may be implemented primarily in hardware using, for example, hardware components, such as application specific integrated circuits (ASICs). Implementation of the hardware state machine so as to perform the functions described herein will be apparent to persons skilled in the relevant art(s).

In yet another example, aspects presented herein may be implemented using a combination of both hardware and software. For example, such hardware may comprise ultrasound scanning equipment.

Figure 10:
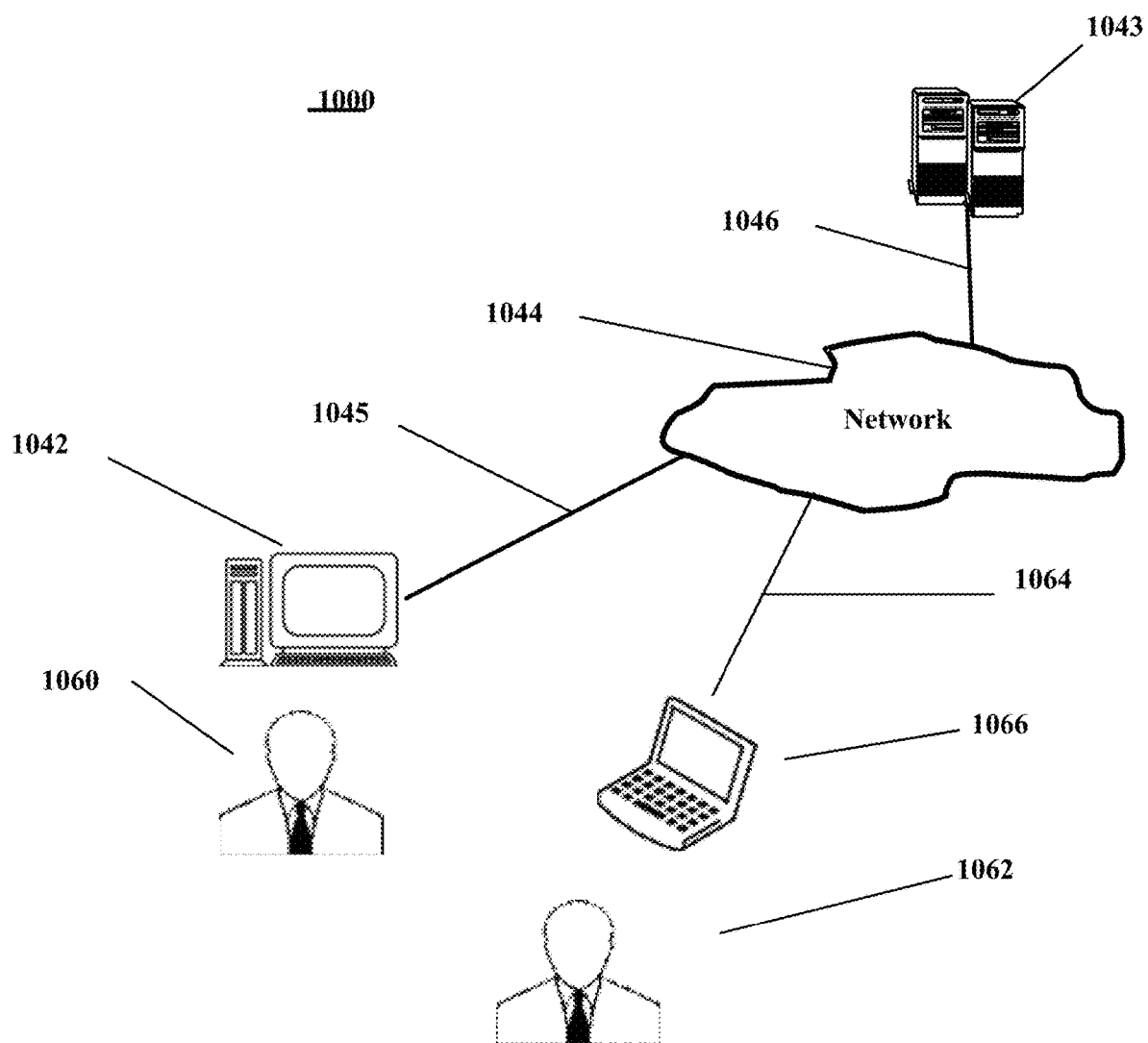
FIG. 10 is a block diagram of various example system components, in accordance with aspects of the present invention.

FIG. 10 is a block diagram of various example system components, for use in accordance with aspects presented herein. FIG. 10 shows a communication system 1000 usable in accordance with the present invention. The communication system 1000 includes one or more accessors 1060, 1062 (also referred to interchangeably herein as one or more "users") and one or more terminals 1042, 1066. In one aspect, data for use in accordance aspects presented herein, for example, input and/or accessed by accessors 1060, 1064 via terminals 1042, 1066, such as personal computers (PCs), minicomputers, mainframe computers, microcomputers, telephonic devices, or wireless devices, such as personal digital assistants ("PDAs") or a hand-held wireless devices coupled to a server 1043, such as a PC, minicomputer, mainframe computer, microcomputer, or other device having a processor and a repository for data and/or connection to a repository for data, via, for example, a network 1044, such as the Internet or an intranet, and couplings 1045, 1046, 1064. The couplings 1045, 1046, 1064 include, for example, wired, wireless, or fiberoptic links. In another aspect, the method and system presented herein operate in a stand-alone environment, such as on a single terminal.

Additional aspects regarding ultrasound are described in attachment 1 and in "Understanding Ultrasound Physics,"

Third Edition by Sindey K. Edelman, the entire contents of which are incorporated herein by reference.

Additional details can be found in Attachment 1.

It is understood that the specific order or hierarchy of steps in the processes disclosed are an illustration of example approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects." Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

The invention claimed is:

1. A method of predicting a level of meat tenderness of a plurality of livestock using an on-the-hoof ultrasound image, comprising:
   receiving, via a communication interface at a central processing location, on-the-hoof ultrasound image of muscle for each of the plurality of livestock from one or more remote devices;
   determining a relative number of muscle bundles and a relative size of the muscle bundles for each of the plurality of livestock using at least one processor at the central processing location that correlates striations in a corresponding ultrasound image for each of the plurality of livestock to the relative number of muscle bundles and the relative size of the muscle bundles from the corresponding ultrasound image for each of the plurality of livestock;
   generating, via the at least one processor at the central processing location, a tenderness rating representing a predicted degree of muscle tissue tenderness for each of the plurality of livestock based on the determined relative number of muscle bundles and the relative size of the muscle bundles in the corresponding ultrasound image, wherein the at least one processor generates a higher tenderness rating for livestock having a larger relative number of the muscle bundles and a smaller relative size of the muscle bundles and a lower tenderness rating is generated for livestock having a smaller relative number of the muscle bundles and a larger size of the muscle bundles, and wherein the at least one processor correlates the predicted degree of the muscle tissue tenderness to an objective shear force value;
   scaling, via the at least one processor, the tenderness rating for each of the plurality of livestock based on at least one of a breed, a sex, an age, or a size of a respective livestock;
   designating, via the at least one processor, the tenderness rating for each of the plurality of livestock;
   using the predicted degree of the muscle tissue tenderness based on a muscle structure in the corresponding ultrasound image for each of the plurality of livestock to predict a final carcass quality of each of the plurality of livestock; and
   transmitting, via the communication interface, tenderness rating data to one or more remote terminals, a report that identifies a subset of the plurality of livestock having a more favorable predicted final carcass quality and the tenderness rating data identifying a subset of the plurality of livestock having the higher predicted level of meat tenderness.

2. The method of claim 1, wherein the report comprises an additional predicted muscle tissue characteristic for each of the plurality of livestock based on the muscle structure in the corresponding ultrasound image, wherein the additional predicted muscle tissue characteristic comprises at least one of a tissue pliability characteristic, a tissue density characteristic, and a tissue strength characteristic.

3. The method of claim 2, wherein the additional predicted muscle tissue characteristic comprises a strength characteristic that predicts an ability of the corresponding livestock to perform in an athletic or competition event.

4. The method of claim 1, wherein determining the relative number of muscle bundles in the corresponding on-the-hoof ultrasound image for the plurality of livestock comprises at least one of:
   determining a percentage of muscle bundles in each on-the-hoof ultrasound image for the plurality of livestock,
   determining a density of the muscle bundles in each on-the-hoof ultrasound image for the plurality of livestock, and
   determining a ratio of the muscle bundles in each on-the-hoof ultrasound image for the plurality of livestock.

5. The method of claim 4, wherein an animal is selected for breeding from among the plurality of livestock based on the corresponding on-the-hoof ultrasound image for the animal further having at least one of:
- a highest percentage of the muscle bundles from among the plurality of livestock,
- a highest density of the muscle bundles from among the plurality of livestock, and
- a highest ratio of the muscle bundles from among the plurality of livestock.

6. The method of claim 1, wherein the higher predicted level of muscle tenderness is predicted for livestock from the plurality of livestock having at least one of smaller bundles, smaller fascicles, or smaller fibers than a corresponding threshold number, and the lower level of muscle tenderness is predicted for livestock from the plurality of livestock having at least one of larger bundles, larger fascicles, or larger fibers than the corresponding threshold number.

7. The method of claim 1, wherein the predicted degree of the muscle tissue tenderness is further based on:
- a relative number of fascicles in a bundle strand from the on-the-hoof ultrasound image.

8. The method of claim 7, wherein the relative number of the fascicles in the bundle is determined based on at least one of:
- a percentage of the fascicles in the bundle,
- a density of the fascicles in the bundle,
- a size of the fascicles in the bundle, and
- a ratio of muscle bundles using the on-the-hoof ultrasound image.

9. The method of claim 1, wherein the predicted degree of the muscle tissue tenderness is further based on
- a relative number of fibers from the on-the-hoof ultrasound image.

10. The method of claim 9, wherein the relative number of fibers is determined based on at least one of:
- a percentage of the fibers in the from the on-the-hoof ultrasound image,
- a density of the fibers in the from the on-the-hoof ultrasound image,
- a size of the fibers in the from the on-the-hoof ultrasound image, and
- a ratio of the fibers in the from the on-the-hoof ultrasound image.

11. The method of claim 1, further comprising:
determining a relative number of fascicles, a relative number of fibers, and a relative number of sarcomeres in the corresponding on-the-hoof ultrasound image for each of the plurality of livestock,
wherein the tenderness rating for each of the plurality of livestock is further based on at least one of the relative number of fascicles, the relative number of fibers, and the relative number of sarcomeres in the corresponding on-the-hoof ultrasound image.

12. The method of claim 1, further comprising:
determining, via the at least one processor at the central processing location, a thickness of a sheath and a matrix of the sheath surrounding the muscle structure in the corresponding on-the-hoof ultrasound image for each of the plurality of livestock, wherein the at least one processor generates the tenderness rating further based on the thickness of the sheath and the matrix of the sheath.

13. The method of claim 1, wherein the tenderness rating is further based on at least one of a maturity and fat measurements for the corresponding livestock from among the plurality of livestock.

14. The method of claim 1, further comprising:
using genetic testing in combination with the predicted degree of the muscle tissue tenderness for each of the plurality of livestock based on the muscle structure in the corresponding ultrasound image to group the subset of the plurality of livestock for breeding.

15. The method of claim 1, further comprising:
generating and outputting to a display, via the at least one processor, the generated tenderness rating for each of the plurality of livestock.

16. The method of claim 1, further comprising:
identifying, via the at least one processor at the central processor location, the subset of the plurality of livestock for breeding, the subset having the higher predicted level of the meat tenderness.

17. The method of claim 16, further comprising:
receiving anticipated breeding results for each of the plurality of livestock; and
comparing the predicted degree of the muscle tissue tenderness for each of the plurality of livestock to a corresponding anticipated breeding result for the corresponding livestock to verify the anticipated breeding results.

18. The method of claim 16, further comprising:
selecting an animal for breeding, from among a group associated with a highest muscle tenderness grade, wherein each of the animals in the group are determined to have a higher predicted degree of the meat tenderness from the generated tenderness rating from among the plurality of livestock.

19. The method of claim 18,
wherein a higher predicted tenderness rating is provided for the subset of the plurality of livestock having finer muscle structure with a higher relative number of smaller muscle bundles,
wherein a lower predicted tenderness rating is provided for the subset of the plurality of livestock having a coarser muscle structure with a lower relative number of larger muscle bundles, and
wherein the animal selected for the breeding has the higher predicted tenderness rating.

20. The method of claim 18,
wherein the higher predicted level of the muscle tenderness is predicted for livestock from the plurality of livestock having at least one of bundle density, fascicle density, or fiber density greater than a corresponding threshold density number,
wherein the lower predicted level of the muscle tenderness is predicted for livestock from the plurality of livestock at least one of the bundle density, the fascicle density, or the fiber density lower than the corresponding threshold density number, and
wherein the animal selected for the breeding is predicted to have the higher predicted level of the muscle tenderness.

21. The method of claim 18, wherein the animal is selected for breeding from among the group based on a corresponding on-the-hoof ultrasound image for the animal having at least one of a highest relative number of the muscle bundles and a smallest relative size of the muscle bundles from among the plurality of livestock.

22. The method of claim 16, further comprising:
grouping the plurality of livestock into a plurality of groups based on the tenderness rating that is generated based on the relative number of the muscle bundles and the relative size of the muscle bundles in the ultrasound image for each of the plurality of livestock, each group being associated with a muscle tenderness grade.

23. The method of claim 22, wherein the grouping includes grouping the subset of the plurality of livestock into a group for breeding purposes, and wherein the group is associated with the muscle tenderness grade that is predicted to have a highest level of the meat tenderness based on the relative number of the muscle bundles and the relative size of the muscle bundles in the corresponding ultrasound image for each of the subset of the plurality of livestock.

24. The method of claim 1, further comprising:
storing, in memory, ultrasound image data for the plurality of livestock to generate historical ultrasound image data.

25. The method of claim 24, further comprising:
selecting an animal for breeding, from among a group associated with a highest muscle tenderness grade; and
using the historical ultrasound image data to identify an inherited muscle structure trend for multiple livestock.

26. The method of claim 1, further comprising:
determining, via the at least one processor at the central processing location, crosslinking of connective tissue from the ultrasound image for each of the plurality of livestock, wherein the at least one processor generates the tenderness rating for each of the plurality of livestock further based on the crosslinking of the connective tissue for the respective livestock.

27. The method of claim 1, further comprising:
measuring, via the at least one processor at the central processing location, a matrix of myofibril from the ultrasound image for each of the plurality of livestock, wherein the at least one processor generates the tenderness rating for each of the plurality of livestock further based on the measured matrix of the myofibril for the respective livestock.

28. The method of claim 1, further comprising:
measuring, via the at least one processor at the central processing location, an area between the muscle structure from the ultrasound image for each of the plurality of livestock, wherein the at least one processor generates the tenderness rating for each of the plurality of livestock further based on the measured area between the muscle structure for the respective livestock.

29. The method of claim 1, wherein the at least one processor at the central processing location designates the tenderness rating for each of the plurality of livestock as an additional rating level to a United States Department of Agriculture (USDA) quality grade rating or a yield grade rating.

30. The method of claim 1, further comprising:
transmitting to the one or more remote terminals, via the communication interface, a recommended cooking technique for a cut of meat based on an analysis of ultrasound image data associated with the cut of meat.

31. The method of claim 1, wherein the generating the tenderness rating for each of the plurality of livestock is performed by the at least one processor based, at least in part, on stored historical data.

* * * * *